(12) United States Patent
Imayama et al.

(10) Patent No.: US 10,266,835 B2
(45) Date of Patent: Apr. 23, 2019

(54) AGROBACTERIUM BACTERIUM TO BE USED IN PLANT TRANSFORMATION METHOD

(71) Applicant: JAPAN TOBACCO INC., Tokyo (JP)

(72) Inventors: Teruyuki Imayama, Kanagawa (JP); Yukoh Hiei, Shizuoka (JP); Yuji Ishida, Shizuoka (JP)

(73) Assignee: JAPAN TOBACCO INC., Tokyo (JP)

(*) Notice: Subject to any disclaimer, the term of this patent is extended or adjusted under 35 U.S.C. 154(b) by 550 days.

(21) Appl. No.: 14/779,875

(22) PCT Filed: Mar. 27, 2014

(86) PCT No.: PCT/JP2014/058926
§ 371 (c)(1),
(2) Date: Sep. 24, 2015

(87) PCT Pub. No.: WO2014/157541
PCT Pub. Date: Oct. 2, 2014

(65) Prior Publication Data
US 2016/0083737 A1    Mar. 24, 2016

(30) Foreign Application Priority Data

Mar. 29, 2013 (JP) ................................ 2013-072177

(51) Int. Cl.
C12N 15/74 (2006.01)
C12N 15/79 (2006.01)
C12N 15/82 (2006.01)

(52) U.S. Cl.
CPC ....... *C12N 15/8205* (2013.01); *C12N 15/743* (2013.01); *C12N 15/79* (2013.01)

(58) Field of Classification Search
CPC ... C12N 15/743; C12N 15/8205; C12N 15/79
See application file for complete search history.

(56) References Cited

U.S. PATENT DOCUMENTS

2009/0075358 A1* 3/2009 Jefferson ............ C12N 15/8202
435/252.3

FOREIGN PATENT DOCUMENTS

WO    WO 00/18939 A1    4/2000
WO    WO 2007/148819 A1    12/2007

OTHER PUBLICATIONS

Van der Fits et al (Plant Molecular Biology, 43: 495-202, 2000) (Year: 2000).*
Tait et al (Gene 20:39-49, 1982) (Year: 1982).*
Hood et al (Transgenic Research 2: 208-218, 1993). (Year: 1993).*
Amoah et al., "Factors influencing *Agrobacterium*-mediated transient expression of uidA in wheat inflorescence tissue," J. Exp. Bot. (May 2001) vol. 52, No. 358, pp. 1135-1142.
An et al. (1988). "Binary vectors," Plant Molecular Biology Manual A3, S.B. Gelvin and R.A. Schilperoort, eds (Dordrecht: Kluwer Academic Press), pp. 1-19.
Arokiaraj et al., "The supervirulence plasmid pToK47 from Agrobacterium tumefaciens A281 improves transformation efficiency of *Hevea brasiliensis*," Am. J .Biochem. Biotechnol. (2009), vol. 5, No. 3, pp. 137-141.
Bevan, M., "Binary *Agrobacterium* vectors for plant transformation," Nucleic Acids Res. (1984) vol. 12, No. 22, pp. 8711-8721.
Christie, P. J., "Type IV secretion: the *Agrobacterium* VirB/D4 and related conjugation systems," Biochim. Biophys. Acta. (Nov. 11, 2004), vol. 1694 (1-3), pp. 219-234.
Citovsky et al., "Single-stranded DNA binding protein encoded by the virE locus of *Agrobacterium tumefaciens*," Science (April 22, 1988), vol. 240, pp. 501-504.
Close et al., "Molecular characterization of the virC genes of the Ti plasmid," J. Bacteriol. (Jun. 1987) vol. 169, No. 6, pp. 2336-2344.
Ditta et al., "Broad host range DNA cloning system for Gram-negative bacteria: Construction of gene bank of *Rhizobium meliloti*," Proc. Natl. Acad. Sci. USA (Dec. 1980), vol. 77, No. 12, pp. 7347-7351.
Dong, S. and R. Qu, "High efficiency transformation of tall fescue with *Agrobacterium tumefaciens*," Plant Sci. (2005), vol. 168, pp. 1453-1458.
Extended European Search Report dated Aug. 30, 2016, in European Patent Application No. 14773265.5.
Fraley et al., "Expression of bacterial genes in plant cells," Proc. Natl. Acad. Sci. USA (Aug. 1983), vol. 80, 4803-4807.

(Continued)

*Primary Examiner* — Lee A Visone
(74) *Attorney, Agent, or Firm* — Birch, Stewart, Kolasch & Birch, LLP

(57) ABSTRACT

This invention relates to the *Agrobacterium* bacterium to be used in plant transformation method comprising three types of plasmids. The *Agrobacterium* bacterium of this invention comprises plasmids of (1) to (3) shown below:

(1) a plasmid comprising the following components:
  (i) the virB gene, the virC gene, the virD1 gene, the virD2 gene, the virD3 gene, the virG gene and the virJ gene of pTiBo542, and
  (ii) an origin of replication;

(2) a disarmed Ti plasmid or a disarmed Ri plasmid of *Agrobacterium* bacterium; and (3) a plasmid having a T-DNA region consisting of a desired DNA;

wherein each of the plasmids of (1) to (3) has a replication mechanism that enables a mutual coexistence with each other.

12 Claims, 10 Drawing Sheets
(1 of 10 Drawing Sheet(s) Filed in Color)
Specification includes a Sequence Listing.

(56) References Cited

OTHER PUBLICATIONS

Fraley et al., "The SEV system: a new disarmed Ti plasmid vector for plant transformation," Biotechnology (Jul. 1985), vol. 3, 629-635.
Hamilton et al., "Stable transfer of intact high molecular weight DNA into plant chromosomes," Proc. Natl. Acad. Sci. USA (Sep. 1996), vol. 93, pp. 9975-9979.
Hellens et al., "A guide to *Agrobacterium* binary Ti Vectors," Trends in Plant Science (Oct. 2000), vol. 5, No. 10, pp. 446-451.
Hellens et al., "pGreen: a versatile and flexible binary Ti vector for *Agrobacterium*-mediated plant transformation," Plant Mol. Biol. (2000), vol. 42, pp. 819-832.
Hepburn et al., "The use of pNJSOOO as an intermediate vector for the genetic manipulation of *Agrobacterium* Ti-plasmids," J. Gen. Microbiol. (1985), vol. 131, pp. 2961-2969.
Hiei et al., "Efficient transformation of rice (*Oryza sativa* L.) mediated by *Agrobacterium* and sequence analysis of the boundaries of the T-DNA," Plant J. (1994), vol. 6, No. 2, pp. 271-282.
Hiei, Y. and T. Komari, "Improved protocols for transformation of indica rice mediated by *Agrobacterium tumefaciens*," Plant Cell Tissue Organ Cult. (2006), vol. 85, 271-283.
Hiei, Y., and T. Komari, "*Agrobacterium*-mediated transformation of rice using immature embryos or calli induced from mature seed," Nat. Protocols (2008), vol. 3, No. 5, pp. 824-834.
Hoekema et al., "A binary plant vector strategy based on separation of vir- and T-region of the *Agrobacterium tumefaciens* Ti-plasmid," Nature (May 12, 1983), vol. 303, 179-180.
Hood et al., "New *Agrobacterium* helper plasmids for gene transfer to plants," Transgenic Res. (1993), vol. 2, pp. 208-218.
Hood et al., "The hypervirulence of *Agrobacterium tumefaciens* A281 is encoded in a region of pTiBo542 outside of T-DNA," J. Bacteriol. (Dec. 1986), vol. 168, No. 3, pp. 1291-1301.
International Preliminary Report on Patentabiiity and Written Opinion dated Jun. 17, 2014, in PCT International Application No. PCT/JP2014/058926, with English translation.
International Search Repon dated Jun. 17, 2014, in PCT International Application No. PCT/JP2014/058926, with English translation.
Ishida et al., "*Agrobacterium*-mediated transformation of maize," Nat. Protocols (Jun. 21, 2007), vol. 2, No. 7, pp. 1614-1621.
Ishida et al., "High efficiency transformation of maize (*Zea mays* L.) mediated by *Agrobacterium tumefaciens*," Nat. Biotechnol. (Jun. 1996), vol. 14, pp. 745-750.
Jefferson, R. A. "Assaying chimeric genes in plants: the GUS gene fusion system," Plant Mol. Biol. Rep. (1987), vol. 5, No. 1, pp. 387-405.
Jin et al., "Genes responsible for the supervirulence phenotype of *Agrobacterium tumefaciens* A281," J. Bacteriol. (Oct. 1987), vol. 169, No. 10, pp. 4417-4425.
Jouanin et al., "Structure of T-DNA in plants regenerated from roots transformed by *Agrobacterium rhizogenes* strain A4," Mol. Gen. Genet. (1987), vol. 206, pp. 387-392.
Khanna, H. K. and G. D. Daggard, "*Agrobacterium tumefaciens*-mediated transformation of wheat using a superbinary vector and a polyamine-supplemented regeneration medium," Plant Cell Rep (2003), vol. 21, 429-436.
Komari et al., "Physical and functional map of supervirulent *Agrobacterium tumefaciens* tumor-inducing plasmid pTiBo542," J. Bacteriol. (Apr. 1986), vol. 166, No. 1, pp. 88-94.
Komari et al., "Vectors carrying two separate T-DNAs for co-transformation of higher plants mediated by *Agrobacterium tumefaciens* and segregation of transformants free from selection markers," Plant J. (1996), vol. 10, No. 1, pp. 165-174.
Komari, T., "Genetic characterization of double-flowered tobacco plant obtained in a transformation experiment," Theor. Appl. Genet. (1990), vol. 80, pp. 167-171.
Koncz, C. and J. Schell, "The promoter of $T_L$ DNA gene 5 controls the tissue-specific expression of chimaeric genes carried by a novel type of *Agrobacterium* binary vector," Mol. Gen. Genet. (1986), vol. 204, pp. 383-396.
Lazo et al., "A DNA transformation-competent *Arabidopsis* genomic library in *Agrobacterium*," Biotechnology (Oct. 1991), vol. 9, pp. 963-967.
Lee, L.-Y., and S. B. Gelvin, "T-DNA binary vectors and systems," Plant Physiol. (Feb. 2008), vol. 146, pp. 325-332.
McBride, K. E. and K. R. Summerfelt, "Improved binary vectors for *Agrobacterium*-mediated plant transformation," Plant Mol. Biol. (1990), vol. 14, pp. 269-276.
Okumura, M. S. and C. I. Kado, "The region essential for efficient autonomous replication of pSa in *Escherichia coli*," Mol. Gen. Genet. (1992), vol. 235, pp. 55-63.
Palanichelvam et al., "A second T-region of the soybean-supervirulent chrysopine-type Ti plasmid pTiChry5, and construction of a fully disarmed vir helper plasmid," Mol. Plant Microbe Interact (2000), vol. 13, No. 10, pp. 1081-1091.
Pantoja, et al., "*Agrobacterium* type IV secretion is a two-step process in which export substrates associate with the virulence protein VirJ in the periplasm," Mol. Microbiol. (2000) vol. 45, No. 5, pp. 1325-1335.
Potrykus et al. (1997). "Genetic engineering of crop plants," Agricultural Biotechnology, A. Altman, ed (NY: Mercel Dekker Inc.), pp. 119-159.
Ream, W. (2008). "Production of a mobile T-DNA by *Agrobacterium tumefaciens*," *Agrobacterium*, T. Tzfira and V. Citovsky, eds (New York: Springer Science+Business Media, LLC), pp. 280-313.
Saito et al., "Cucumber mosaic virus-tolerant transgenic tomato plants expressing a satellite RNA," Theor. Appl. Genet. (1992), vol. 83, pp. 679-683.
Sun et al., "A highly efficient transformation protocol for Micro-Tom, a model cultivar for tomato functional genomics," Plant Cell Physiol. (2006), vol. 47, No. 3, pp. 426-431.
Tang, W. "Additional virulence genes and sonication enhance *Agrobacterium tumefaciens*-mediated loblolly pine transformation," Plant Cell Rep. (2003), vol. 21, pp. 555-562.
Tao, Q. and H.-B. Zhang, "Cloning and stable maintenance of DNA fragments over 300kb in *Escherichia coli* with conventional plasmid-based vectors," Nuc. Acids Res. (1998), vol. 26, No. 21, pp. 4901-4909.
Vergunst et al. "Positive charge is an important feature of the C-terminal transport signal of the VirB/D4-translocated proteins of *Agrobacterium*," Proc. Nat. Acad. Sci. USA (Jan. 18, 2005), vol. 102, No. 3, pp. 832-837.
Ward et al., "Characterization of the virB operon from an *Agrobacterium tumefaciens* Ti plasmid," J. Biol. Chem. (Apr. 25, 1988), vol. 263, No. 12, pp. 5804-5814.
Watson et al., "Plasmid required for virulence of *Agrobacterium tumefaciens*," J. Bacteriol. (Jul. 1975), vol. 123, No. 1, pp. 255-264.
Wenck et al., "High-efficiency *Agrobacterium*-mediated transformation of Norway spruce (*Picea abies*) and loblolly pine (*Pinus taeda*)," Plant Mol. Biol. (1999), vol. 39, pp. 407-416.
Winans et al., "A gene essential for *Agrobacterium* virulence is homologous to a family of positive regulatory loci," Proc. Natl. Acad. Sci. USA (Nov. 1986), vol. 83, pp. 8278-8282.
Wu et al., "Efficient and rapid Agrobacterium-mediated genetic transformation of durum wheat (*Triticum turgidum* L. var. *durum*) using additional virulence genes," Transgenic Res. (2008), vol. 17, pp. 425-436.
Zambryski et al., "Ti plasmid vector for the introduction of DNA into plant cells without alteration of their normal regeneration ability," EMBO J. (1983), vol. 2, No. 12, pp. 2143-2150.

* cited by examiner

GV2260  GV3850  LBA4404
(pLC41GWH-IG)  (pLC41GWH-IG)  (pLC41GWH-IG)

```
                         SEQUENCE LISTING

<160> NUMBER OF SEQ ID NOS: 5

<210> SEQ ID NO 1
<211> LENGTH: 20978
<212> TYPE: DNA
<213> ORGANISM: Artificial Sequence
<220> FEATURE:
<223> OTHER INFORMATION: pVGW9 vector

<400> SEQUENCE: 1
aaaatgcatg gcatgtttaa ccgaatctga cgttttccct gcaaatgcca aaatactatg      60
cctatctccg ggtttcgcgt gacggccaag acccggaaaa ccaaaaatac ggtttgctcg     120
aatacgcgaa cgccaaaggc ttcgcgccgc tacagatcga ggaagaaatt gccagcagag     180
caaaggactg gcgcaagcgc aagctcggag caatcatcga aaaggccgag cgtggcgacg     240
tgctactgac gccggagatt acgcgcattg ccggttccgc cctcgccgcc ttggaaattc     300
tcaaagcggc gagcgagcgc ggcctaatcg tccatgtgac caaacagaag atcatcatgg     360
acggcagcct acaaagcgac atcatggcaa ccgtgcttgg cttggctgca cagatcgagc     420
ggcatttcat tcaggcacgt accaccgagg cgctacaagt cgccagagag cgcggcaaga     480
cgctcgggcg acccaagggc agcaaatcga gcgccttgaa gctggacagc cgtattgatg     540
aagtacaggc atacgtgaac cttggcttgc gcaaagtcg cgcagccgag ttgttaggcg     600
tcagccctca caccttgcgc ctgttcatca aacgccggaa catcaaaccc acaaacacta     660
gaccaaccat caccatgccg gggagggaac aacatgccta agaacaacaa agcccccggc     720
catcgtatca acgagatcat caagacgagc ctcgcgctcg aaatggagga tgcccgcgaa     780
gctggcttag tcggctacat ggcccgttgc cttgtgcaag cgaccatgcc ccacaccgac     840
cccaagacca gctactttga gcgcaccaat ggcatcgtca ccttgtcgat catgggcaag     900
ccgagcatcg gcctgcccta cggttctatg ccgcgcacct tgcttgcttg gatatgcacc     960
gaggccgtgc gaacgaaaga ccccgtgttg aaccttggcc ggtcgcaatc ggaatttcta    1020
caaaggctcg gaatgcacac cgatggccgt tacacggcca cccttcgcaa tcaggcgcaa    1080
cgcctgtttt catccatgat ttcgcttgcc ggcgagcaag gcaatgactt cggcattgag    1140
aacgtcgtca ttgccaagcg cgcttttcta ttctggaatc ccaagcggcc agaagatcgg    1200
gcgctatggg atagcaccct caccctcaca ggcgatttct tcgaggaagt cacccgctca    1260
ccggttccta tccgaatcga ctacctgcat gccttgcggc agtctccgct tgcgatggac    1320
atttacacgt ggctgaccta tcgcgtgttc ctgttgcggg ccaagggccg cccttcgtg    1380 caaatccctt gggtcgccct gcaagcgcaa ttcggctcat cctatggcag ccgcgcacgc    1440
aactcgcccg aactggacga taaggcccga gagcgggcag agcgggcagc actcgccagc    1500
ttcaaataca acttcaaaaa gcgcctacgc gaagtgttga ttgtctatcc cgaggcaagc    1560
gactgcatcg aagatgacgg cgaatgcctg cgcatcaaat ccacacgcct gcatgtcacc    1620
cgcgcacccg gcaagggcgc tcgcatcggc cccctccga cttgaccagg ccaacgctac    1680
gcttggcttg gtcaagcctt cccatccaac agcccgccgt cgagcgggct ttttatccc    1740 cggaagcctg tggatagagg gtagttatcc acgtgaaacc gctaatgccc cgcaaagcct    1800
tgattcacgg ggctttccgg cccgctccaa aaactatcca cgtgaaatcg ctaatcaggg    1860
```

```
tacgtgaaat cgctaatcgg agtacgtgaa atcgctaata aggtcacgtg aaatcgctaa    1920 tcaaaaggc acgtgagaac gctaatagcc ctttcagatc aacagcttgc aaacacccct     1980
cgctccggca agtagttaca gcaagtagta tgttcaatta gcttttcaat tatgaatata    2040
tatatcaatt attggtcgcc cttggcttgt ggacaatgcg ctacgcgcac cggctccgcc    2100
cgtggacaac cgcaagcggt tgcccaccgt cgagcgcctt tgcccacaac ccggcggccg    2160
caacagatcg ttttataaat tttttttttt gaaaagaaa aagcccgaaa ggcggcaacc     2220
tctcgggctt ctggatttcc gatcaacgca ggagtcgttc ggaaagtagc tgttccagaa    2280
ttataggcgc agagacacca gattccaaga tggctctgtt aaattgttgt agtatgtagt    2340
atcatacaac atactacagt acagaggccc gcaagaatgg caatcactaa acaagacatt    2400
tggcgagcag ccgacgaact ggacgccgaa ggcatccggc ccactttggc cgccgtgcgc    2460
aagaaactcg gaagcggtag cttcacaacc atttccgatg caatggctga atggaaaaac    2520
cgcaagaccg ccaccctgcc ctcatcagac ccattgccgg ttgcagtcaa cgagcatctt    2580
gccgagcttg gcaatgcgct atgggctatc gccctggcgc acgccaacgc ccggtttgac    2640
gaagatcgga aacagatcga ggccgacaaa gcggccatca gccagcagct tgccgaagca    2700
atcgaactag ccgacacctt cacccgcgaa aacgaccagc tccgcgaacg agtagatccc    2760
aaaaactagt cagagccacc ccatcaggaa tatcgcccat tccgtcatca gcgtggtgac    2820
gtgcatcagg cgcgcttgtt gcagaacttt aagtgcttct ttcgattcga gatctcagca    2880
aaagttctcc gcaaaccttc accgcgggct tacgtgtctt ttgtaacaaa ttgcgacgca    2940
gttgatatcc acttgaaaca ttagtccgaa attatcgaga tctccgctga taaggtatcg    3000
aaatggcgat aaaattggta ttgatactcg tattcacact cttccccgcg gcagacgctg    3060
catatgcgaa tgaccgcgcc aacggtttca tgtggtcaaa cggggcgaa actggagtga    3120 ggcttcctct tcgggtgttc aatgccaagc cagccaagaa cacggtggcg atcatttatt    3180
ccggagacgc tggatggcaa aatatcgatg aggcgattgg tacctatctg cagacggaag    3240
ggattcctgt cattggcgtc agttcacttc ggtatttctg gtcggagcgg tccccaagcg    3300
aaactgctaa ggatcttggt cacataatcg atgtctacac caagcatttc ggtgtgcaga    3360
atgttttact tgtaggatat tctttcggcg cggacgtcat gccggcaagc ttcaataggc    3420
ttacgcttga gcaaaaaaat cgggttaagc aaatctctct cttggcattg tcacatcaag    3480
tcgactatgt cgtctcattt aggggctggc tccaactcga aacggaaggt aagggcggca    3540
atcctctgga tgatctcaga tccattgacc ctgcaatcgt ccaatgcatg tacgggcgcg    3600
aagaccgtaa taatgcttgc ccatctctcc gacagaccgg cgcagaggtg ataggcttca    3660
gcggaggcca tcactttgat aatgatttca aaaaactgtc tacgcgcgtc gtctcaggcc    3720
tcgtggcacg cctaagtcat cagtaatctt tagttcctgc accgctttag tattgactgg    3780
gatagcgacg cctgtgatgc agacatcgga tattgtgtcg ttaagtaaaa ggccttcgtc    3840
tgatcgcgag actcgctagt ggttttcagg tgagtgagat gttttgccgc aagttgcgct    3900
gagatcgcat ctgcctgcgg ctgccgcacc tccagattgg cagcaacaag atcatccttc    3960
aagggaagat gcctataacg catgtgttga cgactttcgc ctcgtgaatg atccggtctg    4020
ttcccgacag tgggatgccg tcgcgataga gcaggctctc gcgccaggag gaatttctcc    4080
gatatgactt ctctccttct acgtgcccaa agcagcaacg aaatcatcta tcgcggccaa    4140
aagagcggtc atgtgaaagc acccttgcca gtcaattccc tggccaaggt cagcacggcg    4200
```

```
atactgcgag gtgttgctac accacggagg cgatctagaa ggacgatttc atcatttagg      4260
ccgcacactc ataaatcagg tttgcaaatc ggtctgattt tgattcattg aggcttgact      4320
tggaggccac tgataacccg tccccgcttt gatgtcaccg atttcgaatg gactgttgtt      4380
cagtcctttg ttcccaaata agccgcgtcg cgtgccgcgc gttgacgcgg gtgatcaatg      4440
tcatcttgtg gcgcttccgg acgggcccgc cctgggcaga cgttcctgat cgatacggtt      4500
cctgtacaac ctgctacaat cgctttgtac gatggcgtga ggcagacgtc tgggatcata      4560
ttctgagtgt gatttccaag gctttcgata gaatgtcgtc atgattgaca gttcctgtgt      4620
ccgcgtccac caacatgcgg cgacgggaaa cagcgggatc aagacgatgg ctgtatggga      4680
cgttcccgtg gcggtttgac caccaagatt cacgctgttg tcgatgccga cggttgaccg      4740
atccgtcttg cgctgacagc gggtcaagcc catgaccgcc gcatgaccga acattttta      4800 caaataatcg cttagagtgc gtttctgctg gcggacaagg catatgatac caacgcgata      4860
agagcatttg caaagcgcaa gcaggcatgg gccaatattc ctgccaagag caatcggaag      4920
gaagcttccc gttcatcgaa tgggtttaca gacagcgtaa cctcgccgag cattttcgtt      4980
ctgagcctga cctgaccaac tgcggcctga ataggtcgat ccggttgctt agtcatggat      5040
gcgcggttct cggtccatgt tgcgttccaa gacgccgggc gaggtttctc gcttcaattg      5100
aaatcataaa gaagcaattg aaaattttcg agtaaccgac cctcccgata atcttcaaca      5160
taaaacaacg cacttcttcc aacgggagag gcggtgttag ttgcgagcta aggagataag      5220
gtatgcttaa gagatcgggg tcgctttctc ttgccttgat ggtctccttc tgttcgtcga      5280
gccttgccac gccactctca tctgctgagt ttgaccatgt tgctcgcaag tgtgccccat      5340
cagttgcgac atctacgctt gcggcgatag ctaaggtgga gagtcgcttt gatcctttag      5400
cgattcatga caacacgacc ggcgaaacgc ttcactggca agatcacagc caagcaaccc      5460
aagtcgtcag gcaccgtctc gatgcacggc attcgctgga tgttggcctc atgcaaataa      5520
actctcgaaa ttttctatg ctcggtctga cacctgacgg tgcgctccag gcgtgcacat      5580
cattatctgc cgctgcaaac atgctgaaaa gtcgttatgc aggcggcgaa acgattgacg      5640
agaagcaatt tgcgcttcgt cgggcgatct ccgcttacaa caccggtaat ttcatcggcg      5700
gttttgcaaa cggctacgtg cgaaaagttg aaacagctgc tcaatcgctg gtgcccgcgt      5760
taatcgagcc tccaaaagac gatcacgagg cgctaaaatc cgaagagacg tgggatgttt      5820
gggggtcata tcagcgccgc tcgcaggagg atggcgctgg cggtttaatc gctccgccac      5880
cgccacacca ggacaacggc aaatccgcag acgacaatca agtcttattc gacttatact      5940
aaggaggtgc gcattgatgc gatgctttga gagataccgt ttacatctaa atcgcctctc      6000
gctctcgaat gcgatgatgc gcgtgatatc gagctgcgcc ccaagcttgt gcggtgcaat      6060
tgcatggagc atttcctcat ccggacccgc cgcagcgcaa tctgcgggtg gcggcactga      6120
ccccgccaca atggttaaca atatatgcac gtttatcctt ggtccgttcg gccagtcact      6180
cgctgttctc ggcattgtcg ctatcgggat ctcctggatg ttcgggcggg cttcgcttgg      6240
gctggttgcc ggcgtcgtcg gcggcattgt tatcatgttt ggggcgagct tcctcggcca      6300
aacgctcact ggcggtagtt gatggctgat cgtttggaag aatcgaccct ttacctcgca      6360
gccacacggc ccgcattgtt tcttggggtg ccactgacat tggcagggtt attcatgatg      6420
ttcgccggct ttgtcatcgt tatcgttcag aacccgctct acgaagtcgt tctcgtgccg      6480
ttatggtttg cagcccggct catcgtggag cgagactaca atgcggcgag cgtcgtcctg      6540
ctatttttgc ggaccgcggg aagaagcatt gatagtgcag tttgggggggg cgctactgtt      6600
```

```
agcccaaatc caattagggt tcccccacga gggagaggaa tggtgtgatg ctcggcgcga   6660
gtggaacgac cgaaagatcc ggtgagatct atctcccttta tattggccac ctcagcgacc   6720
atatcgtcct tcttgaagac ggatcgatca tgaccattgc gagaattgat ggcgttgcat   6780
tcgagcttga ggaaactgaa atgcgcaatg cgcgttgtcg tgcgttcaac acgctgttgc   6840
gcaatatcgc tgatgatcat gtgtcaatat atgctcacct cgtacgtcat gccgacgtgc   6900
catcatcggc gccgcgacac ttccgtagtg ttttcgccgc tagcctgaac gaagcttttg   6960
aacagcgcgt gctctccggc caactcctcc gcaatgaaca cttccttacg ttgattgtct   7020
acccacaggc ggctttaggg aaggtaaaga ggaggttcac caagctaagc ggaaaaaggg   7080
aaaacgatct cacgggccag atcaggaaca tggaagatct ttggcatgtt gtcgctggct   7140
ctcttaaagc gtatggcctg catcgtcttg gcatccgcga aagcagggt gtgctcttca    7200 ccgaaattgg cgaagcgcta cggttgatca tgactggtcg gttcacaccg gttccggtcg   7260
tcagcggctc actcggcgct tcgatttata ccgacagagt catttgcggc aagcgaggac   7320
tcgagatcag aacgccaaaa gacagttacg ttggatccat ctattcgttt cgcgaatacc   7380
ctgcaaaaac acgccgggc atgctcaacg cgctgctatc cctcgatttt ccacttgttc    7440
tcacgcagag ttttcgttc ctgactcgcc cgcaagcgca cgcgaaactt agcctcaaat     7500
cgagccagat gctgagttcc ggcgataaag ccgtgactca aatcggcaaa ttatccgagg   7560
ctgaggacgc acttgcgagc aacgaattcg ttatggctc acatcatttg agcctttgcg    7620
tctatgcaga cgatctcaat agtcttgggg acaggggcgc gcgggctcgg acacgaatgg   7680
cggatgcagg tgccgtggtt gtccaagaag gtattggtat ggaagcggcc tattggtccc   7740
aattgccggg gaattttaag tggcgcacac gccctggcgc aatcacttca cgcaatttcg   7800
cagggtttgt ctctttcgaa aacttttccag agggcgccag ctcaggccac tggggcaacg   7860
cgattgcccg atttcgtacc aatggcggaa cgcctttcga ctatatcccg catgagcacg   7920
atgttggcat gacggcaata ttcgggccta tcgggagggg taagacgacg ctcatgatgt   7980
ttgttctagc catgctcgaa cagagcatgg tcgaccgtgc aggtacggtc gtgttctttg   8040
acaaggaccg gggtggcgaa ttgctggttc gcgccacagg aggaacatat ttggcacttc   8100
acagaggcac acccagcggg ttggcgccgt tgcgtggcct agaaaacaca gcagcctcac   8160
acgattttct gcgcgaatgg atcgtggctc tcatcgagag tgatggtcgg ggtgggattt   8220
ctccggaaga gaaccgccgt ctggtccgtg gtatccatcg tcagctctcg tttgatccac   8280
aaatgcgttc aatcgcgggg ttacgtgaat ttttgttgca tgggcccgcc gaaggcgcag   8340
gagcgcggct ccaacgctgg tgccggggcc atgcgcttgg ctgggcattt gacggcgaag   8400
ttgacgaagt aaagttagat ccgtcgatta ccggcttcga catgacgcat cttctcgaat   8460
acgaggaagt atgcgctccc gctgcagcat atctcctgca tcggattgga gccatgatcg   8520
acggccgccg ttttgtgatg agctgcgatg agtttcgcgc ctatttgtta aaccctaaat   8580
tttcgactgt cgtcgacaaa ttcctcctga ccgttcgaaa aaacaacggg atgctaatac   8640
tggcaacgca gcaaccagag catgttctgg aatcgccgct aggagccagc ttggttgcgc   8700
aatgtatgac gaagattttc tatccatcac caaccgcaga tcgatcggct tatgtcgatg   8760
gactgaaatg taccgaaaag gaatttcagg cgatccgtga agacatgacg gtcggcagcc   8820
gtaagttctc tcttaaacga gaaagtggaa gcgtcatctg cgaatttgat ctgcgggata   8880
tgcgtgaata tgtcgccgtg ctttcggggc gtgccaacac ggtgcgcttt gcaactcgac   8940
```

```
tacgcgaggc acaagaaggc aactcatctg gctggctcag cgaattcatg gcccgtcacc    9000
acgaggcaga agattgataa ggtaggaaac gatgaagacg acgcaactta ttgcaacagt    9060
tttgacctgc agctttctat atattcagcc cgcgcgggcg cagtttgttg ttagcgaccc    9120
ggcaacggag gctgagacgc tcgcgactgc gctcgcgact gcggagaatc tcactcagac    9180
tatagcgatg gttacgatgt tgacgtcggc ctacggcgtt actggactac tgacttcgct    9240
caaccagaaa aatcagtatc cttcgacgaa ggacctagac aatgaaatgt tttgccgcg    9300 aatgccaatg tcgaccacgg cacgtgcgat caccagcgat acagatcgtg cagtcgtggg    9360
tagtgatgct gaagcggacc tgttgcgatc gcagatcacc ggttccgcaa acagcgctgg    9420
cattgcggct gacaatctgg aaacgatgga caaacgcttg acggcgaatg ctgatacgtc    9480
tgctcagctt tcccgatctc gcaatatcat gcaggcaacc gtgaccaatg gtttgcttct    9540
caagcagatc catgacgcaa tgattcaaaa tgtacaggcg acaagcctat taacgatgac    9600
taccgcgcag gccggccttc acgaggcgga agaggcggcc gctcaacgca aggagcatca    9660
aaagaccgct gtcatctttg gtgccctccc ctaaggctgg gcgatttgtt catccgcccg    9720
catcctcgcc gaatgcgagc tcattttatc caacattatg cgacaaacca gtcaagttca    9780
ggtccaatcg atgaatttca cgattccggc gccgtttacg gccattcata cgatcttcga    9840
tgtagccttc acgacaggct tggactcgat gcttgagact atccaggagg cggtgagtgc    9900
gccattgatc gcctgtgtca ctctttggat tattgttcag ggtattttag tcatacgcgg    9960
cgaagtcgat acccgtagcg gtatcactcg ggtgatcacg gtcaccatcg ttgttgctct    10020
aattgttggg caggctaact accaagacta tgtggtttcc atcttcgaaa agacggtccc    10080
aaactttgtt cagcagttta gtgtaaccgg cttgcctctg cagactgttc cggcacagtt    10140
ggatacaatg ttcgccgtga cccaggccgt ttttcagaaa atcgcatccg aaatcggtcc    10200
gatgaacgac caggacatcc ttgctttcca aggggcacag tgggtccttt acggcacgct    10260
ctggtctgcc ttcggagttt acgacgccgt tggaattctc acgaaagtgc ttctcgcgat    10320
cgggcctctg atcctcgtcg gatatatttt tgatcgcacg cgggacatcg cagctaagtg    10380
gatcgggcaa cttatcacct acggtctctt gcttctcctc ttaaacctcg tggcaacgat    10440
cgtcatccta accgaagcga ctgcgctcac ccttatgctt ggtgtaatca ccttcgccgg    10500
tacgaccgcg gccaagatca ttggtcttta cgaactcgat atgttttttc tgacaggga    10560 tgcgctcatt gtcgctttgc cggcgatcgc cggcaacatt ggaggcagtt actggagcgg    10620
cgcaacccaa tctgccagca gcttgtaccg tcgcttcgct caggttgagc gaggctaggt    10680
cgcgcaaaaa ttcgcctcaa tggagaattc tatgaagtat tgcctgctgt gcctagttgt    10740
cgctttgagc ggctgccaga caaacgacac attagcgagc tgcaaaggcc cgatcttccc    10800
gctgaatgtg gggcgatggc agcctactcc gtcagatctt cagctcggca attcgggtgg    10860
acgctatgac ggggcctgaa tatgccatgc tagtggcgcg cgaaagcctt gccgagcact    10920
ataaggaagt agaagccttt caaaccgcgc gagcgaaatc ggcgcgacgt ctctccaaac    10980
tcattgcagc tgtcgcagct atcgcgattt tgggaaatgt tgctcaagcg ttcgctatag    11040
ccacaatggt gccgttgagc aggcttgtgc ccgtatatct atggatacgg ccggacggca    11100
ccgttgacag cgaggtgtct gtctcgcgat tgcctgcaac tcaagaggag gccgtcgtta    11160
acgcctcatt gtgggagtac gttcgcctgc gcgagagtta tgatgccgac accgctcagt    11220
acgcctacga cctggtatcg aacttcagtg ccccaacagt gcgccaggat taccagcaat    11280
tcttcaacta tcccaatccc agttcgcctc aagtcattct tggcaaacgc ggcagggtgg    11340
```

```
aggtcgagca catcgcttca aatgatgtaa ctccaagcac gcagcaaatt cgctataaaa    11400
ggaccctcgt cgttgacggc aaaatgcctg tggtgagtac gtggaccgcg acagttcgct    11460
acgaaaaggt gaccagcttg cccggcagat tgagactaac caacccggca ggtctggttg    11520
tcacctccta tcagacatcg gaagataccg tttcaaacgt aggccacagc gaaccatgat    11580
cagaaaagca cttttcattt tagcatgttt atttgccgct gcgactggtg cggaggctga    11640
agacactcca atggcgggca agctagatcc gcgcatgcgt tatttggctt acaatcccga    11700
tcaagtggtg cgcctctcga cggcggttgg agctactttg gtcgtaacat tcgccacgaa    11760
cgaaacggtg acagcggttg ccgttttcaaa tagcaaagat ctagcagccc taccgcgggg    11820
aaattatcta tttttcaagg caagccaggt cctcacgcct cagccagtaa tcgtgctaac    11880
cgcaagcgac tccgggatgc gccgttatgt tttcagtata agttccaaga ctctgtccca    11940
cctcgataaa gagcagcccg atctctatta cagcgtccaa ttcgcctacc ccgccgacga    12000
tgcggcggct cggcgaaggg aggcacaaca gaaggctgtt gtggacagac tacacgcgga    12060
agcacaatat caacggaaag ctgagaattt attggatcag cctgtcacag cccttggtgc    12120
ggcggacagt aattggcact acgtcgccca aggcgatcgt tcgctgttgc cactcgaagt    12180
cttcgacaat ggatttacga cggtattcca ctttccgggc aatgtacgca taccctccat    12240
ctacaccatc aatcctgatg gcaaggaagc tgttgccaac tattcagtta aagggagcga    12300
tgtcgagatt tcttcggttt cccgaggttg gcgtctgagg gatggccaca cagtactatg    12360
tatctggaac accgcttacg atcccgttgg ccaaaggccg caaacgggca cggtgaggcc    12420
cgatgtgaaa cgcgtcctga agggggcgaa gggatgaata acgatagtca gcaagcggca    12480
catgaggttg atgcatctgg atccctggtc tccgacaaac atcgccggcg tctttcgggg    12540
tctcagaaat tgatcgtcgg aggtgtcgtt ctcgcgttat cattaagcct catttggcta    12600
ggtgggcgcc aaaagaaggt gaatgagaac gcatcgccgt caactttgat cgcaacaaac    12660
accaagccat tcatccagc tccgattgag gtgccgccgg atcctccagc ggttcaagag    12720
gctgttcagc ctgctgctcc tctaccgccg aggggcgaac cggagcggca tgagccacgg    12780
ccggaagaaa caccgatttt tgcatatagc agcggcgatc aaggggtcag caaacgcgcc    12840
attcagggcg acacgggccg aagacaagaa ggcaagcgtg acgacaactc cttgccgaat    12900
ggcgaagtgt ccggcgagaa cgatttgtcg atacgtatga aacccaccga gctgcagccc    12960
agcagcgcca cgctcttgcc gcaccccgat tttatggtaa cgcaagggac aataattccg    13020
tgcatcttgc aaaccgcaat cgacacaaat ttggcaggct atgtaaagtg tgtcttgcct    13080
caggatattc gtggaacaac gaacaatatc gtgcttcttg atcgtggcac caccgttgtt    13140
ggcgaaatac agcgtggctt gcaacaggga gatgggcgcg ttttgtgtt gtgggatcgc    13200 gccgagacac ctgaccatgc gatgatctcg ttaacatcgc caagcgcgga cgaactcggt    13260
cgctcaggat tgccgggctc ggtcgacagc cacttctggc agcgttttag cggagctatg    13320
ctcttgagtg ttgttcaagg cgccttccag gcagctagca cctacgccgg cagctcgggt    13380
ggcgggatga gcttcaacag ctttcaaaat aacggtgagc agacaactga gacagccctt    13440
aaggcaacca tcaacatacc gccaaccctg aagaagaatc agggtgacac cgtttccatt    13500
ttcgtagcac gggacctcga tttctttggt gtttaccagc tccgcctgac tggcggcgcc    13560
acgcggggga ggaaccgccg ctcttaatga attcaaattt ccgcttagag ataggataca    13620
ttgtaaatgg aagtggatcc gcaactacgc tttcttctga agccgatttt ggaatggctc    13680
```

```
gatgacccga agactgaaga aattgcgatc aatcgacctg gagaggcatt tgtgcgccaa    13740
gccggcattt ttaccaagat gcctttgccc gtctcttatg atgatcttga agatatcgct    13800
attttagcgg gcgcgctgag aaagcaggat gtcggaccac gtaaccccct ctgcgccact    13860
gaacttcctg gtggtgaacg actacaaatc tgtctgccgc cgaccgttcc ctcgggcacc    13920
gtcagcttga ccattcgacg gccaagctcg cgtgtttctg gtcttaaaga agtctcctcc    13980
cgttatgatg cttcgaggtg gaaccagtgg cagacacgaa ggaaacgcca aaatcaggat    14040
gatgaagcta tccttcagca ttttgacaac ggggatttgg aagcgtttct gcacgcatgc    14100
gtcgtcagcc gactgacgat gttgctatgt ggccctaccg gaagcggcaa gacaacaatg    14160
agcaagacct tgatcagcgc catccccccc caggaaaggc taatcaccat agaagatacg    14220
ctcgaactcg tcattccaca cgataatcat gttagactac tctactccaa gaacggtgct    14280
gggctgggtg ctgtgagcgc cgagcacttg ctccaagcaa gtctgcgtat gcggccggac    14340
cggatattgc ttggcgagat gcgcgacgat gcagcatggg cttatctgag tgaagtcgtc    14400
tcgggacatc cggatcgat ttcaacaata cacggcgcga atccaatcca aggattcaag    14460
aaactgtttt cccttgtcaa aagtagcgcc caaggtgcta gcttggaaga tcgcacactg    14520
attgacatgc tctctacggc gatcgatgtc atcattccat tccgtgccta tgaggacgtt    14580
tatgaagtag gcgagatctg gctcgcggcg gacgcacgac gccggggcga gaccataggc    14640
gatctcctta atcaatagta gctgtaacct cgaagcgttt cacttgtaac aacgattgag    14700
aacttttgtc ataaaattga aatacttggt tcgcattttc gtcatccgcg gtcagccgca    14760
attctgacga actgcccatt tagctggaga tgattgtaca tccttcacgt gaaaatttct    14820
caagcgctgt gaacaagggt tcagatttta gattgaaagg tgagccgttg aaacacgttc    14880
ttcttatcga tgacgatgtc gctatgcggc atcttattat cgaataccatt acgatccacg    14940 ccttcaaagt gaccgcggta gccgacagca cccagttcac tagagtactc tcttccgcga    15000
cggtcgatgt cgtggttgtt gatctaaatt taggtcgtga agatgggctt gagatcgttc    15060
gaaatctggc ggcaaagtct gatattccaa tcataattat cagtggcgac cgccttgagg    15120
agacggataa agttgttgca ctcgagctag gagcaagtga ttttatcgct aagccgttta    15180
gtacgagaga gtttcttgca cgcattcggg ttgccttgcg cgtgcgcccc aacgttgtcc    15240
gctccaaaga ccgacggtct ttttgtttta ctgactggac acttaatctc aggcaacgtc    15300
gcttgatgtc cgaagctggc ggtgaggtga aacttacggc aggtgagttc aatcttctcc    15360
tcgcgttttt agagaaaccc cgcgacgttc tatcgcgcga gcaacttctc attgccagtc    15420
gagtacgcga cgaggaggtt tacgacagga gtatagatgt tctcattttg cggctgcgcc    15480
gcaaacttga ggcggatccg tcaagccctc aactgataaa aacagcaaga ggtgccggtt    15540
atttctttga cgcggacgtg caggtttcgc acgggggggac gatggcagcc tgagccaatt    15600
gcatttggct cttaattatc tggctcaaaa ggtgactgag gacgcggcca gcggcctcaa    15660
acctacactc aatatttggt gagggggttcc gataggtccc tcttcaccaa ttgctcgatg    15720
gcttctctcc agcaaagaat gacgcgagcg cggcggtagc cagcttgtgg ccgaaagctc    15780
gagcggtctc caaccccaac ggatcaaaat gacttcgagc gacctcgagc aacgcaaccg    15840
ggaacatgcg tgaggtctga acgagaacgg attttttctgt agttgaaggg atcggataac    15900
ttttcggggc cacgcgaaat gatccatctg ccagcatgct ttcgaaatcg tccaacgcgc    15960
gccttaaaat catttgtagc gacttcgagg gactgtattg ccgaacgagg ttgtcatatg    16020
ttttcgacac ttgaggcgcg ggcggtcgcg ctgaaagaaa aacctggagc tttttcgggg    16080
```

```
acggaggtgg actaagggca tccacagtta gcttaagttg tcgatcggga ctgtaaatgt   16140
gatcggcgac gagaggctca cgttgctggt ctttctcgtc ggcttttca ggcaagtgct    16200 ggaggtccag cttctgggga acaagtgtcg ggttgggatg gtggatctcg ggtcgagcac   16260
cagcaagccg ccgtgcttcg ccgaccgaca atgcgggctt cgaattgcc atcttcaagc    16320 ctccaagatt ttgctgatca gtttcgaaat gaccacgact tcctccatcg caatccgaag   16380
attcctctct atgaggcgca tcgtcggatc agttcccgtg tttagtaatg taagatgcaa   16440
catgccgcgt tctttcatcg cggcaaatgc atctctttca tgcatgggag acggtacaac   16500
tggaaggctc tctagcgtct ctgacatcct gcgttgcgat gttgtcaatc ggccgaccgg   16560
gacgcgttgg cgcaaaacag ctgtaggaat tgccaaattt tcactcaaca gcagctcgat   16620
gacgtagcgg taggtagata gtgcctcatc gatgtcgagc ggcgttagca tggtggggat   16680
cagaagcagg tttgagctag cgatgattgt gttgttgagc tcgctcgagc cgccacgcgt   16740
atcggccaac gcataatcaa atccttcgag ctcggcattt tcataggctg cttcaagaag   16800
gggcatttcg tcggcggaat agacttcaca gcgaggatcc caggtactgc tttgtaaggc   16860
gttttctctc catcgcgtca gaggccggtt tcgtcggca tcaaagaggg ccactcgttt    16920
accgtcattt gccaaagcag cgcaaaggcc catgagtgcg gtggttttgc cagcaccccc   16980
tttgaaagaa caaacgtca aaagttgcat attctgatcc cgcctatcct gtgaaaccgg    17040
agtgcatttg tattttttgtt cgtataaatg ttttttgtgat tatcgatgag taaaagcgtt  17100
gttacactat ttttatttca cattcgttat aagacaattg caaatgtagc aagtatattc   17160
agtattgact gtaaatgtac tgttgatttc atattgagca gggctagact tccatccgtc   17220
tacccgggca catttcgtgc tggagtatcc agaccttccg ctttctttgg aggaagctat   17280
gtcaaaacac accagagcca cgtcgagtga gactaccatc aaccagcatc gatccctgaa   17340
agttgaaggg ttcaaggtcg tgagtgcccg tctgcgatcg gccgagtatg aaaccttttc   17400
ctatcaagcg cgcctgctgg gactttcgga tagtatggca attcgcgttg cggtgcgccg   17460
catcgggggc tttctcgaaa tagatgcaga cacacgagaa aagatggaag ccatacttca   17520
gtccatcgga atactctcaa gcaatgtatc catgcttcta tctgcctacg ccgaagaccc   17580
tcgatcggat ctggaggctg tgcgagatga acgtattgct tttggcgagg ctttcgccgc   17640
cctcgatgga ctactgcgct ccattttgtc cgtatcccgg cgacggatcg acggtcgctc   17700
gttactgaaa ggtgccttgt agcacttgac cacgcacctg acgggagaaa attggatgcc   17760
cgatcgcgct caagtaatca ttcgcattgt gccaggaggt ggaaccaaga cccttcagca   17820
gataatcaat cagctggagt acctgtcccg aaagggaaag ctggaactgc agcgttcagc   17880
ccggcatctc gatattcccg ttccgccgga tcaaatccgt gagcttgccc aaagctgggt   17940
tacggaggcc gggatttatg acgaaagtca gtcagacgat gacaggcaac aagacttaac   18000
aacacacatt attgtaagct tccccgcagg taccgaccaa accgcagctt atgaagcaag   18060
ccgggaatgg gcagccgaga tgtttgggtc aggatacggg ggtggccgct ataactatct   18120
gacagcctac cacgtcgacc gcgatcatcc acatttacat gtcgtggtca atcgtcggga   18180
acttctgggg caggggtggc tgaaaatatc caggcgccat ccccagctga attatgacgg   18240
cttacggaaa aagatggcag agatttcact tcgtcacggc atagtcctgg atgcgacttc   18300
gcgagcagaa aggggaatag cagagcgacc aatcacatat gctgaatatc gacgccttga   18360
gcggatgcag gctcaaaaga ttcaattcga agatacagat tttgatgaga cctcgcctga   18420
```

```
ggaagatcgt cgggacctca gtcaatcgtt cgatccattt cgatcggacg catctgccgg    18480
cgaaccggac cgtgcaaccc gacatgacaa acaaccgctt gaaccgcacg cccgtttcca    18540
ggagcccgcc ggctccagca tcaaagccga cgcacggatc cgcgtaccat ggagagcga     18600 gcggggtgcc caaccatccg cgtccaaaat ccctgtaact gggcatttcg ggattgagac    18660
ttcgtatgtc gctgaagcca gcgtgcccaa acaaagcggc aattccgata cttctcgccc    18720
ggtgactgac gttgccatgc acacagtcga gcgccagcag cgatcaaaac gacgtcatga    18780
cgaggaggca ggtccgagcg gagcaaaccg taaaagattg aaggccgcgc aagttgattc    18840
cgaggcaaat gtcggtgagc ccgacggtcg cgatgacagc aacaaggcgg ctgatccggt    18900
gtctgcttcc atccgtaccg agcaaccgga agcttctcca acgtgtccgc gtgaccgtca    18960
cgatggagaa ttgggagaac gcaaacgtgc aagaggtaat cgtcgcgacg atgggcgcgg    19020
ggggacctag agacaggaag gaccgaataa tggcaaatgg tcagttcacg atacgctctg    19080
ctcgcccggc ctccgtcgga ctgacaggcg aacggcgtgg agccgcatcc gcctctagct    19140
ctgcactgtc caatgttcaa agagatgtta gggataggct gattccaact agctcaccaa    19200
gattaccaaa tgcagccata ttgcgtgatt cctcgggaag agcgtcgact ggtctgcggt    19260
acatggcggc tactcttcat tggtctgcga tcgcgccatt atcgctaata aacagcaacg    19320
acctggctcc ggccgcttat gactttgaga cgcgaaataa cgcaagaaat gtgactgcca    19380
aagtcggcag ggcagtccct gttcccaagc aaggcgggct cggcaaaacg ctcgcacccg    19440 tacccccttag tacacgtata tcaagggtca attccgaccg aagactgccc gctgacgcag    19500
aagaccgccc tgaaacgcgc gaccccccaga aggacgtgg cagtcatggt gcgacgccaa    19560
ccttacatga aaagattgga accgcgtttg ctcgaagatt gcgaaagcat acgtactata    19620
ttgtttgcag ttgctgccag acccggagcg cgttgacgat gggtgcaaag atttcggtga    19680
agtcatgaac tccagcaaga cttcgcccca gcgtatgacc ctgagcatcg tatgttcgct    19740
ggcagccggt ttttgtgcgg ccagctgcta tgtaacgttc cgccggggct tcaacgcgca    19800
agcgatgatg acgttcgacg ttttcgcttt ttggtatgag accccgcttt acttgggtta    19860
tgccagcacc gtcttctggc gtggtttatc tgttgtcatc tttacctcgc tgatcgttct    19920
ttcaagtcag ctcatcatat cgctgcgcaa tcagaagcat catgggacag ctcgttgggc    19980
agaaattggc gaaatgcggc atgctggtta tctgcagcgt tacagtcgca tcaaggggcc    20040
gatctttgga gggttgacat aagcctgttc ggttcgtaaa ctgtaatgca agtagcgtat    20100
gcgctcacgc aactggtcca gaaccttgac cgaacgcagc ggtggtaacg gcgcagtggc    20160
ggttttcatg gcttgttatg actgtttttt tgtacagtct atgcctcggg catccaagca    20220
gcaagcgcgt tacgccgtgg gtcgatgttt gatgttatgg agcagcaacg atgttacgca    20280
gcagcaacga tgttacgcag cagggcagtc gccctaaaac aaagttaggt ggctcaagta    20340
tgggcatcat tcgcacatgt aggctcggcc ctgaccaagt caaatccatg cgggctgctc    20400
ttgatctttt cggtcgtgag ttcggagacg tagccaccta ctcccaacat cagccggact    20460
ccgattacct cgggaacttg ctccgtagta agacattcat cgcgcttgct gccttcgacc    20520
aagaagcggt tgttggcgct ctcgcggctt acgttctgcc caagtttgag cagccgcgta    20580
gtgagatcta tatctatgat ctcgcagtct ccggcgagca ccggaggcag ggcattgcca    20640
ccgcgctcat caatctcctc aagcatgagg ccaacgcgct tggtgcttat gtgatctacg    20700
tgcaagcaga ttacggtgac gatcccgcag tggctctcta tacaaagttg gcatacgggc    20760
aagaagtgat gcactttgat atcgacccaa gtaccgccac ctaacaattc gttcaagccg    20820
```

```
agatcggctt cccggccgcg gagttgttcg gtaaattgct agctttaagg gcgaattctg    20880
cagatatcca tcacactggc ggccgctcga gcatgcatct agagggccca attcgcccta    20940
tagtgagtcg tattacaatt cactggccgt cgttttac                            20978
```

```
<210> SEQ ID NO 2
<211> LENGTH: 29
<212> TYPE: DNA
<213> ORGANISM: Artificial Sequence
<220> FEATURE:
<223> OTHER INFORMATION: PCR primer pSa5'EcT22I

<400> SEQUENCE: 2
aaaatgcatg gcatgtttaa cagaatctg                                      29

<210> SEQ ID NO 3
<211> LENGTH: 16
<212> TYPE: DNA
<213> ORGANISM: Artificial Sequence
<220> FEATURE:
<223> OTHER INFORMATION: PCR primer M13(-20)Fw

<400> SEQUENCE: 3
gtaaaacgac ggccag                                                    16

<210> SEQ ID NO 4
<211> LENGTH: 60
<212> TYPE: DNA
<213> ORGANISM: Artificial Sequence
<220> FEATURE:
<223> OTHER INFORMATION: PCR primer pTiBo542:150641Fw

<400> SEQUENCE: 4
aaaaactagt cagagccacc ccatcaggaa tatcgcccat tccgtcatca gcgtggtgac    60

<210> SEQ ID NO 5
<211> LENGTH: 44
<212> TYPE: DNA
<213> ORGANISM: Artificial Sequence
<220> FEATURE:
<223> OTHER INFORMATION: PCR primer delD2-3'Rv

<400> SEQUENCE: 5
tccaaagatc ggccccttga tgcgactgta acgctgcaga taac                     44
```

AGROBACTERIUM BACTERIUM TO BE USED IN PLANT TRANSFORMATION METHOD

TECHNICAL FIELD

The present application claims priority based on Japanese Patent Application No. 2013-072177 submitted on Mar. 29, 2013, and the entire content of the application is incorporated herein by reference.

The present invention relates to *Agrobacterium* bacterium that comprises three types of plasmids and is used in plant transformation, and the use thereof.

BACKGROUND ART

Generally speaking, plant transformation is performed using a technique of introducing foreign DNA into plant cells, which allows the foreign gene to be retained/expressed in progenies of fertile seeds or vegetative propagated plants. Quite a few monocotyledons and dicotyledons were actually transformed using the technique. Not only were crops of maize, rice, wheat, barley, sorghum, soybean, rapeseed, sunflower, cotton, potato, tomato produced by plant transformation, but those of fruits and other vegetables were also produced, and a strong interest exists for the commercial use of the technique.

Publicly known plant transformation methods include physical/chemical methods such as polyethylene glycol, electroporation, particle gun, etc. (direct introduction of DNA) and biological methods using the function of the *Agrobacterium* bacterium (indirect introduction of DNA). The direct introduction of DNA is often associated with problems such as fragmentation of the target gene during introduction, and an introduction of a high number of copies. As a result, there is a frequent occurrence of transformed plants that do not express the target gene or transformed plants that show weak, abnormal expression (gene silencing). A use of protoplasts in a method prolongs the culture period, which tends to induce non-fertile seeds or malformation in the obtained transformants as a result of mutations during culture. In contrast, such problems are unlikely to occur when the gene is introduced by the *Agrobacterium* bacterium. In the method using *Agrobacterium*, the target gene is introduced via regulating expression of the gene group of the virulent region of the Ti or Ri plasmid (vir region). The target gene is introduced into the plant by the work of the protein group encoded in the vir gene, going through many processes including recognizing the interaction and signaling between plant cells and bacterium, inducing expression of the vir gene, creating a Type IV secretion route, recognizing the T-DNA border repeat sequences, creating the T-DNA strand, and transferring the T-DNA strand to the plant cell and then to the nucleus, and integrating the T-DNA into the plant nucleus genome. Such process restrains the number of introduced copies of the target gene and prevents the gene from being fragmented in introduction. As a result, it was possible to prolifically and stably produce transformed plants exhibiting a high expression of the target gene, so that the variation in the population of transformation products is lower than the direct introduction of DNA.

As seen, *Agrobacterium* method is quite suitable for plant transformation, but actually, the success and efficiency of plant transformation vary greatly according to the plant species, the genotypes and the plant tissue types that are used (Potrykus et al., 1997). There are still many plants that cannot be transformed with sufficient efficiency, and at the current stage, the crops for which a large number of transformed plants can be provided are limited. There is thus a strong need for improved methods to solve such problem.

Many vectors for transformation have been developed to date in an effort to solve the above problems. The background of vector development is explained below. Conventionally, the large size of the Ti plasmid of a wild-type *Agrobacterium* at 190 kb or longer made it difficult to use the standard gene engineering method to insert genes into the T-DNA on the plasmid. Hence, methods were developed to insert foreign genes onto the T-DNA. The following bacterial strains having disarmed Ti plasmids, which are tumor-inducing Ti plasmids whose plant growth regulator synthetic gene is deleted from T-DNA, were first constructed: LBA4404 (Hoekema et al., 1983), GV3850 (Zambryski et al., 1983), GV3TillSE (Fraley et al., 1985), C58-Z707 (Hepburn et al., 1985), GV3101::pMP90 (Koncz and Schell, 1986), GV3101::pMP90RK (Koncz and Schell, 1986), GV2260 (McBride and Summerfelt, 1990), NTI (pKPSF2) (Palanichelvam et al., 2000).

These bacterial strains were used to develop two methods for introducing the desired gene into the T-DNA of a Ti plasmid of *Agrobacterium*, or introducing the other plasmid having the T-DNA with the desired gene into *Agrobacterium*. One of these methods is called an intermediate vector method (Fraley et al., 1983), which allows easy genetic manipulation and insertion of the desired gene, and this method is performed by introducing intermediate vectors that can be replicated by *E. coli* into the T-DNA of disarmed Ti plasmids of *Agrobacterium* by homologous recombination through triparental mating (Ditta et al., 1980). Another method is called the binary vector method, which is based on the finding that the vir region is required for integration of T-DNA into plants but it does not have to be located on the same plasmid as T-DNA to perforin its function (Hoekema et al., 1983) (Lee and Gelvin, 2008). This vir region includes virA, virB, virC, virD, virE and virG. The tern "binary vector" refers to a vector carrying T-DNA integrated into a small plasmid replicable in both *Agrobacterium* and *E. coli*, and this binary vector is introduced into *Agrobacterium* having a disarmed Ti plasmid before use. Introduction of a binary vector into *Agrobacterium* can be accomplished in any known manner, for example, by electroporation or triparental mating. Examples of a binary vector include pBIN19 (Bevan, 1984), pBI121 (Jefferson, 1987), pGA482 (An et al., 1988), etc., and many new binary vectors have been constructed based on these vectors and used for transformation (Lee and Gelvin, 2008).

*Agrobacterium* A281 (Watson et al., 1975) is a super-virulent bacterial strain whose host range is wide, and its transformation efficiency is higher than other strains (Komari et al., 1986). This feature is based on pTiBo542 of Ti plasmid having A281 (Jin et al., 1987).

Three transformation systems that use pTiBo542 have been developed. The first uses bacterial strains that have a disarmed Ti plasmid of pTiBo542, namely, EHA101 (Hood et al., 1986), EHA105 (Hood et al., 1993), AGL0 (Lazo et al., 1991) or AGL1 (Lazo et al., 1991). This system is used as a system with a high transformation ability to transform various plants, and such ability is obtained by applying these strains to the above binary vector system.

The second is a super-binary vector system (Hiei et al., 1994; Ishida et al., 1996). This system is a kind of a binary vector system because it consists of a disarmed Ti plasmid having the vir regions (all of virA, virB, virC, virD, virE and virG, virJ) and a plasmid with T-DNA. However, it differs in that it uses a super-binary vector wherein a 14.8 kb KpnI fragment taken from the pTiBo542 vir region (a part of the virD1 gene, the virB gene, the virC gene and the virG gene) has been introduced into the plasmid with T-DNA, i.e., the binary vector. The KpnI fragment was described to be 15.8 kb in the first article (Jin et al., 1987), but it is 14.8 kb to be correct. Besides, homologous recombination via triparental mating can be used as a convenient technique to introduce the T-DNA region carrying a desired gene into *Agrobacterium* containing a super-binary vector (Komari, 1996). It has now been clarified that the super binary vector system would provide an extremely high transformation efficiency in various plant species (Saito et al., 1992; Hiei et al., 1994; Ishida et al., 1996). In particular, it is reported that the super binary system shows an excellent effect for maize transformation (Ishida et al., 1996). In addition, Khanna and Daggard (2003) was successful in obtaining a wheat transformat that was not obtainable from a combination of LBA4404 and a normal binary vector pHK22 by using a combination of an *Agrobacterium* strain LBA4404 that is not super-virulent and a super binary vector pHK21.

The third is a system in which plasmid pTOK47 (Jin et al., 1987), which is a plasmid carrying a 14.8 kb KpnI fragment (a part of virD1, virB, virC and virG) cut out from the vir region of pTiBo542, is additionally introduced to the binary vector system as a booster vector for improving transformation efficiency. A binary vector system that further includes a booster vector is generally called a "ternary vector system," but the booster vector comprises a 14.8 kb KpnI fragment as mentioned above, so this vector is particularly referred to as the "super-ternary vector system" in the present specification. In this system, plasmids, which can coexist in *Agrobacterium* and have different origins of replication (ori) belonging to different incompatibility groups, are used. Each ori needs a coding region of the Rep protein (initiator), and they are normally used in close proximity. It has been reported that the super ternary vector system using pTOK47 shows a high transformation efficiency in many plant species (Wenck et al., 1999; Tang, 2003; Dong and Qu, 2005; Arokiaraj et al., 2009). The origin of replication (ori) of pTOK47 belongs to the IncW incompatibility group, and the plasmids having T-DNA in the reports of these ternary-vector systems use mainly an ori belonging to the IncP incompatibility group. The super ternary vector system using the booster vector pTOK47 is reported as being useful for the transformation of maize, although somewhat less than the super binary vector system (WO 2007/148819 A1). There is also a report of wheat transformation by using a super ternary vector system, in which a 14.8 kb KpnI fragment derived from the vir region of pTiBo542, similar to pTOK47, is located on a plasmid other than the plasmid with the T-DNA (Amoah et al., 2001; Wu et al., 2008). The vector system used by Amoah et al. (2001) and Wu et al. (2008) consists of pGreen which contains only the IncW ori but lacks the rep gene (Hellens et al., 2000), and pSoup which contains the rep gene of IncW in the trans portion and also contains the oriV of IncP that is necessary for self replication (Hellens et al., 2000). That is, the plasmids pSoup and pGreen are stably maintained in the *Agrobacterium* by pSoup supplementing the replication of pGreen. This system is thus specifically called the dual binary vector system. However, it is actually recognized to be a super ternary vector system consisting of three types of plasmids, the disarmed Ti plasmid, the binary vector pSoup and the ternary vector pGreen.

Knowledge Relating to the Vir Region of pTiBo542

Jin et al. (1987) assessed the crown gall formation ability by retaining super-vir (the vir region of pTiBo542) of various lengths as additional matters in *Agrobacterium*. In the test, the super-virulent strain A281 containing the entire super-vir region was used with the normal strain A348. The result showed that an addition of virB and virG of super-vir is important to improve transformation ability (crown gall formation ability) in both strains. On the other hand, no effect was observed for addition of the virD or virE region (Jin, S., Komari, T., Gordon, M. P., and Nester, E. W. (1987). Genes responsible for the supervirulence phenotype of *Agrobacterium tumefaciens* A281. J. Bacteriol. 169, 4417-4425. Table 3 and FIG. 3).

In addition, Hiei et al (1994) used the disarmed strain EHA101 (pIG121Hm) of the super-virulent strain A281 and a super binary vector LBA4404 (pTOK233) having normal virulence (entire normal vir region) but also retaining a part of the super-vir (virB, virC, virG) on the binary vector to compare their transformation ability concerning rice. As a result, the latter was verified as having a higher transformation efficiency. This suggests that a use of a partial region (virB and virG) provides a higher transformation ability than a use of the entire region when using the transformation vector of the super-vir region.

Concerning virD, virD1 and virD2 cut the border sequence and produce T-DNA. In particular, virD2 forms a complex with T-DNA. virD3 has a low conservative property, and is considered to be unnecessary for the transfer of T-DNA. virD4 constitutes a type IV secretion system together with the virB gene group. virD5 is considered to be an accessory protein having a signal function of type IV secretion system (Ream, W. (2008). Production of a mobile T-DNA by *Agrobacterium tumefaciens*. In *Agrobacterium*, T. Tzfira and V. Citovsky, eds (New York: Springer Science+Business Media, LLC), pp. 280-313.)

Generally speaking, a small vector is more preferable, since incorporation of a desired DNA is easier in a smaller vector. It is also presumed that the foreign DNA that can be stably maintained in *E. coli* is 1200 to 1500 kb per cell (Tao, Q., and Zhang, H.-B. (1998). Cloning and stable maintenance of DNA fragments over 300 kb in *Escherichia coli* with conventional plasmid-based vectors. Nucleic Acids Research 26 4901-4909). As such, *E. coli* cannot stably maintain a plasmid that is larger than a certain size. For example, there are 30 to 40 copies of plasmid having a ColE1-derived origin of replication per an *E. coli* cell, so the *E. coli* cell cannot maintain plasmids that are larger than 30 to 40 kb.

There was no knowledge concerning the vir region of pTiBo542 suggesting that the virD region and the vin region are particularly useful for transformation using the *Agrobacterium* bacterium.

CITATION LIST

Patent Documents

Patent Document 1: WO2007/148819 A1

Non-Patent Documents

Non-Patent Document 1: Amoah, B. K., Wu, H., Sparks, C., and Jones, H. D. (2001). Factors influencing *Agrobacterium*-mediated transient expression of uidA in wheat inflorescence tissue. J Exp Bot 52, 1135-1142

Non-Patent Document 2: An, G., Evert, P. R., Mitra, A., and Ha, S. B. (1988). Binary vectors. In Plant Molecular Biology Manual A3, S. B. Gelvin and R. A. Schilperoort, eds (Dordrecht: Kluwer Academic Press), pp. 1-19

Non-Patent Document 3: Arokiaraj, P., Leelawathy, R., and Yeang, H. Y. (2009). The supervirulence plasmid pTOK47 from Agrobacterium tumefaciens A281 improves transformation efficiency of Hevea brasiliensis. Am J Biochem Biotechnol 5, 137-141

Non-Patent Document 4: Bevan, M. (1984). Binary Agrobacterium vectors for plant transformation. Nucleic Acids Res 12, 8711-8721

Non-Patent Document 5: Christie, P. J. (2004). Type IV secretion: the Agrobacterium VirB/D4 and related conjugation systems, Biochim Biopys Acta 1694, 219-234

Non-Patent Document 6: Citovsky, V., de Vos, G., and Zambryski, P. (1988). Single-stranded DNA binding protein encoded by the virE locus of Agrobacterium tumefaciens. Science 240, 501-504

Non-Patent Document 7: Close, T. J., Tait, R. C., Rempel, H. C., Hirooka, T., Kim, L., and Kado, C. I. (1987). Molecular characterization of the virC genes of the Ti plasmid. J Bacteriol 169, 2336-2344

Non-Patent Document 8: Ditta, G., Stanfield, S., Corbin, D., and Helinski, D. R. (1980). Broad host range DNA cloning system for gram-negative bacteria: construction of gene bank of Rhizobium meliloti. Proc Natl Acad Sci USA 77, 7347-7351

Non-Patent Document 9: Dong, S., and Qu, R. (2005). High efficiency transformation of tall fescue with Agrobacterium tumefaciens. Plant Sci 168, 1453-1458

Non-Patent Document 10: Fraley, R. T., Rogers, S. G., Horsch, R. B., Eicholtz, D. A., and Flick, J. S. (1985). The SEV system: a new disarmed Ti plasmid vector for plant transformation. Biotechnology 3, 629-635

Non-Patent Document 11: Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L., and Woo, S. C. (1983). Expression of bacterial genes in plant cells. Proc Natl Acad Sci USA 80, 4803-4807

Non-Patent Document 12: Hamilton, C. M., Frary, A., Lewis, C., and Tanksley, S. D. (1996). Stable transfer of intact high molecular weight DNA into plant chromosomes. Proc Natl Acad Sci USA 93, 9975-9979

Non-Patent Document 13: Hellens, R. P., Edwards, E. A., Leyland, N. R., Bean, S., and Mullineaux, P. M. (2000). pGreen: a versatile and flexible binary Ti vector for Agrobacterium-mediated plant transformation. Plant Mol Biol 42, 819-832

Non-Patent Document 14: Hepburn, A. G., White, J., Pearson, L., Maunders, M. J., Clarke, L. E., Prescott, A. G., and Blundy, K. S. (1985). The use of pNJ5000 as an intermediate vector for the genetic manipulation of Agrobacterium Ti-plasmids. J Gen Microbiol 131, 2961-2969

Non-Patent Document 15: Hiei, Y., and Komari, T. (2006). Improved protocols for transformation of indica rice mediated by Agrobacterium tumefaciens. Plant Cell Tissue Organ Cult 85, 271-283, pp. 271-283

Non-Patent Document 16: Hiei, Y., and Komari, T. (2008). Agrobacterium-mediated transformation of rice using immature embryos or calli induced from mature seed Nat Protocols 3, 824-834

Non-Patent Document 17: Hiei, Y., Ohta, S., Komari, T., and Kumashiro, T. (1994). Efficient transformation of rice (Oryza sativa L.) mediated by Agrobacterium and sequence analysis of the boundaries of the T-DNA. Plant J 6, 271-282

Non-Patent Document 18: Hoekema, A., Hirsch, P. R., Hooykaas, P. J. J., and Schilperoort, R. A. (1983). A binary plant vector strategy based on separation of vir- and T-region of the Agrobacterium tumefaciens Ti-plasmid. Nature 303, 179-180

Non-Patent Document 19: Hood, E. E., Helmer, G. L., Fraley, R. T., and Chilton, M.-D. (1986). The hypervirulence of Agrobacterium tumefaciens A281 is encoded in a region of pTiBo542 outside of T-DNA. J Bacteriol 168, 1291-1301

Non-Patent Document 20: Hood, E. E., Gelvin, S. B., Melchers, L. S., and Hoekema, A. (1993). New Agrobacterium helper plasmids for gene transfer to plants. Transgenic Res 2, 208-218

Non-Patent Document 21: Ishida, Y., Hiei, Y., and Komari, T. (2007). Agrobacterium-mediated transformation of maize Nat Protocols 2, 1614-1621

Non-Patent Document 22: Ishida, Y., Saito, H., Ohta, S., Hiei, Y., Komari, T., and Kumashiro, T. (1996). High efficiency transformation of maize (Zea mays L.) mediated by Agrobacterium tumefaciens. Nat Biotechnol 14, 745-750

Non-Patent Document 23: Jefferson, R. A. (1987). Assaying chimeric genes in plants: the GUS gene fusion system. Plant Mol. Biol. Rep. 5, 387-405

Non-Patent Document 24: Jin, S., Komari, T., Gordon, M. P., and Nester, E. W. (1987). Genes responsible for the supervirulence phenotype of Agrobacterium tumefaciens A281. J. Bacteriol. 169, 4417-4425

Non-Patent Document 25: Jouanin, L., Guerche, P., Pamboukdjian, N., Tourneur, C., Delbart, F. C., and Tourneur, J. (1987). Structure of T-DNA in plants regenerated from roots transformed by Agrobacterium rhizogenes strain A4. Mol Gen Genet 206, 387-392

Non-Patent Document 26: Khanna, H. K., and Daggard, G. D. (2003). Agrobacterium tumefaciens-mediated transformation of wheat using a superbinary vector and a polyamine-supplemented regeneration medium. Plant Cell Rep 5, 429-436

Non-Patent Document 27: Komari, T. (1990). Genetic characterization of double-flowered tobacco plant obtained in a transformation experiment. Theor Appl Genet 80, 167-171

Non-Patent Document 28: Komari, T., Halperin, W., and Nester, E. W. (1986). Physical and functional map of supervirulent Agrobacterium tumefaciens tumor-inducing plasmid pTiBo542. J Bacteriol 166, 88-94

Non-Patent Document 29: Komari, T., Hiei, Y., Saito, Y., Murai, N., and Kumashiro, T. (1996). Vectors carrying two separate T-DNAs for co-transformation of higher plants mediated by Agrobacterium tumefaciens and segregation of transformants free from selection markers. Plant J 10, 165-174

Non-Patent Document 30: Koncz, C., and Schell, J. (1986). The promoter of TL-DNA gene 5 controls the tissue-specific expression of chimeric genes carried by a novel type of Agrobacterium binary vector. Mol Gen Genet 204, 383-396

Non-Patent Document 31: Lazo, G. R., Stein, P. A., and Ludwig, R. A. (1991). A DNA transformation-competent Arabidopsis genomic library in Agrobacterium Biotechnology 9, 963-967

Non-Patent Document 32: Lee, L.-Y., and Gelvin, S. B. (2008). T-DNA binary vectors and systems. Plant Physiol 146, 325-332

Non-Patent Document 33: McBride, K. E., and Summerfelt, K. R. (1990). Improved binary vectors for Agrobacterium-mediated plant transformation. Plant Mol Biol 14, 269-276

Non-Patent Document 34: Okumura and Kado, (1992) The region essential for efficient autonomous replication of pSa in *Escherichia coli*. Mol Gen Genet 235:55-63

Non-Patent Document 35: Palanichelvam, K., Oger, P., Clough, S. J., Cha, C., Bent, A. F., and Farrand, S. K. (2000). A second T-region of the soybean-supervirulent chrysopine-type Ti plasmid pTiChry5, and construction of a fully disarmed vir helper plasmid. Mol Plant Microbe Interact 13, 1081-1091

Non-Patent Document 36: Pantoja, M., Chen, L., Chen, Y., and Nester, E. W. (2002). *Agrobacterium* type IV secretion is a two-step process in which export substrates associate with the virulence protein VirJ in the periplasm. Mol Microbiol 45, 1325-1335

Non-Patent Document 37: Potrykus, I., Bilang, R., Futterer, J., Sautter, C., and Schrotte, M., and Spangenberg, G. (1997). Genetic engineering of crop plants. In Agricultural Biotechnology, A. Altman, ed (NY: Mercel Dekker Inc.), pp. 119-159

Non-Patent Document 38: Ream, W. (2008). Production of a mobile T-DNA by *Agrobacterium tumefaciens*. In *Agrobacterium*, T. Tzfira and V. Citovsky, eds (New York: Springer Science+Business Media, LLC), pp. 280-313

Non-Patent Document 39: Saito, Y., Komari, T., Masuta, C., Hayashi, Y., Kumashiro, T., and Takanami, Y. (1992). Cucumber mosaic virus-tolerant transgenic tomato plants expressing a satellite RNA. Theor Appi Genet 83, 679-683

Non-Patent Document 40: Sun, H.-J., Uchii, S., Watanabe, S., and Ezura, H. (2006). A highly efficient transformation protocol for Micro-Tom, a model cultivar for tomato functional genomics. Plant Cell Physiol 47, 426-431

Non-Patent Document 41: Tang, W. (2003). Additional virulence genes and sonication enhance *Agrobacterium tumefaciens*-mediated loblolly pine transformation. Plant Cell Rep 21, 555-562

Non-Patent Document 42: Tao, Q., and Zhang, H.-B. (1998). Cloning and stable maintenance of DNA fragments over 300 kb in *Escherichia coli* with conventional plasmid-based vectors. Nuc Acids Res 26, 4901-4909

Non-Patent Document 43: Vergunst, A. C., van Lier, M. C. M., den Dulk-Ras, A., Grosse Stuve, T. A., Ouwehand, A., and Hooykaas, P. J. J. (2005). Positive charge is an important feature of the C-terminal transport signal of the VirB/D4-translocated proteins of *Agrobacterium*. Proc Nat Acad Sci USA 102, 832-837

Non-Patent Document 44: Ward J. E., Akiyoshi D. E., Regier D., Datta A., Gordon M. P., Nester E. W. (1988) Characterization of the virB operon from an *Agrobacterium tumefaciens* Ti plasmid. J Biol Chem 263, 5804-5814

Non-Patent Document 45: Watson, B., Currier, T. C., Gordon, M. P., Chilton, M.-D., and Nester, E. W. (1975). Plasmid required for virulence of *Agrobacterium tumefaciens*. J Bacteriol 123, 255-264

Non-Patent Document 46: Wenck, A. R., Quinn, M., Whetten, R. W., Pullman, G., and Sederoff, R. (1999). High-efficiency *Agrobacterium*-mediated transformation of Norway spruce (*Picea abies*) and loblolly pine (*Pinus taeda*). Plant Mol Biol 39, 407-416

Non-Patent Document 47: Winans, S, C., Ebert, P. R., Stachel, S. E., Gordon, M. P. and Nester, E. W. (1986) A gene essential for *Agrobacterium* virulence is homologous to a family of positive regulatory loci. Proc Natl Acad Sci USA 83, 8278-8282

Non-Patent Document 48: Wu, H., Doherty, A., and Jones, H. D. (2008). Efficient and rapid *Agrobacterium*-mediated genetic transformation of durum wheat (*Triticum turgidum* L. var. *durum*) using additional virulence genes. Transgenic Res 17, 425-436

Non-Patent Document 49: Zambryski, P., Joos, H., Genetello, C., Leemans, J., Van Montagu, M., and Schell, J. (1983). Ti plasmid vector for the introduction of DNA into plant cells without alteration of their normal regeneration ability. EMBO J 2, 2143-2150

SUMMARY OF INVENTION

Technical Problem

*Agrobacterium* is an extremely advantageous method for plant transformation, but the success and the efficiency of transformation vary greatly depending on the plant species, the genotypes and the plant tissue types to be used (Potrykus et al., 1997). There are still many plants that cannot be transformed with sufficient efficiency, and types of crops for which many transformants can be obtained are limited. Hence, an improved method for solving such problems is strongly desired.

The object of the present invention is to provide *Agrobacterium* bacterium using a new super ternary system and a method for plant transformation using such *Agrobacterium* bacterium that enable high efficiency in introducing genes into plants and high transformation efficiency.

Means to Solve Problem

The present invention includes the following Embodiments as preferable Embodiments, without being limited thereby.

[Embodiment 1]

An *Agrobacterium* bacterium comprising plasmids of (1) to (3) shown below:
 (1) a plasmid comprising the following components:
  (i) the virB gene, the virC gene, the virD1 gene, the virD2 gene, the virD3 gene, the virG gene and the virJ gene of pTiBo542, and
  (ii) an origin of replication;
 (2) a disarmed Ti plasmid or a disarmed Ri plasmid of *Agrobacterium* bacterium; and
 (3) a plasmid having a T-DNA region consisting of a desired DNA;
wherein each of the plasmids of (1) to (3) has a replication mechanism that enables a mutual coexistence with each other.

[Embodiment 2]

The *Agrobacterium* bacterium according to Embodiment 1, wherein the origin of replication (ii) of the plasmid (1) is IncW origin of replication.

[Embodiment 3]

The *Agrobacterium* bacterium according to either Embodiment 1 or 2, wherein the plasmid (1) further comprises the virE gene of pTiBo542.

[Embodiment 4]

The *Agrobacterium* bacterium according to any one of Embodiments 1 to 3, wherein the plasmid (1) further comprises the repA gene.

[Embodiment 5]

The *Agrobacterium* bacterium according to any one of Embodiments 1 to 4, wherein the plasmid (1) further comprises a drug selectable marker gene.

[Embodiment 6]
The *Agrobacterium* bacterium according to Embodiment 5, wherein the drug selectable marker gene is a gentamycin resistance gene.

[Embodiment 7]
The *Agrobacterium* bacterium according to any one of Embodiments 1 to 6, wherein the plasmid (1) is pVGW9 having a DNA sequence of SEQ ID NO: 1.

[Embodiment 8]
The *Agrobacterium* bacterium according to any one of Embodiments 1 to 7, wherein the disarmed plasmid of the *Agrobacterium* bacterium (2) is a disarmed Ti plasmid.

[Embodiment 9]
The *Agrobacterium* bacterium according to any one of Embodiments 1 to 8 that does not retain a disarmed pTiBo542.

[Embodiment 10]
The *Agrobacterium* bacterium according to any one of Embodiments 1 to 9 that is produced by introducing the plasmid (1) and the plasmid (3) to the *Agrobacterium* bacterium selected from a group consisting of LBA4404, GV3850, GV3TillSE, C58-Z707, GV3101::pMP90, GV3101::pMP90RK, GV2260, and NTI (pKPSF2).

[Embodiment 11]
An *Agrobacterium* bacterium comprising plasmids of (1) to (2) shown below:
(1) a plasmid comprising the following components:
(i) the virB gene, the virC gene, the virD1 gene, the virD2 gene, the virD3 gene, the virG gene and the virJ gene of pTiBo542, and
(ii) an origin of replication; and
(2) a disarmed Ti plasmid or a disarmed Ri plasmid of *Agrobacterium* bacterium;
wherein each of the plasmid (1) and the plasmid (2) has a replication mechanism that enables a mutual coexistence with each other.

[Embodiment 12]
A method for plant transformation comprising contacting the *Agrobacterium* bacterium of any one of Embodiments 1 to 10 with a plant cell.

[Embodiment 13]
A method for plant transformation comprising:
introducing the plasmid (3) having a T-DNA region consisting of a desired DNA to the *Agrobacterium* bacterium of Embodiment 11; and
contacting the *Agrobacterium* bacterium with a plant cell.

[Embodiment 14]
The method for plant transformation according to Embodiment 12 or 13, wherein the plant is an angiosperm.

[Embodiment 15]
A kit for use in a method for transforming a plant cell by *Agrobacterium*, wherein the kit comprises the *Agrobacterium* bacterium according to any one of Embodiments 1 to 10 or Embodiment 11.

[Embodiment 16]
A kit for use in a method for transforming a plant cell by *Agrobacterium*, wherein the kit comprises a combination of plasmids of (1) to (3) shown below:
(1) a plasmid comprising the following components:
(i) the virB gene, the virC gene, the virD1 gene, the virD2 gene, the virD3 gene, the virG gene and the virJ gene of pTiBo542, and
(ii) an origin of replication;
(2) a disarmed Ti plasmid or a disarmed Ri plasmid of *Agrobacterium* bacterium; and
(3) a plasmid having a T-DNA region consisting of a desired DNA;

wherein each of the plasmids of (1) to (3) has a replication mechanism that enables a mutual coexistence with each other.

[Embodiment 17]
A kit for use in a method for transforming a plant cell by *Agrobacterium*, wherein the kit comprises a combination of plasmids of (1) and (3) shown below:
(1) a plasmid comprising the following components:
(i) the virB gene, the virC gene, the virD1 gene, the virD2 gene, the virD3 gene, the virG gene and the virJ gene of pTiBo542, and
(ii) an origin of replication; and
(3) a plasmid having a T-DNA region consisting of a desired DNA;
wherein each of the plasmids of (1) and (3) has a replication mechanism that enables a mutual coexistence with each other.

[Embodiment 18]
The kit according to Embodiment 17 further comprising the *Agrobacterium* bacterium selected from a group consisting of LBA4404, GV3850, GV3TillSE, C58-Z707, GV3101::pMP90, GV3101::pMP90RK, GV2260, and NTI (pKPSF2).

[Embodiment 19]
A pVGW9 plasmid having the DNA sequence according to SEQ ID NO: 1.

[Embodiment 20]
A use of the plasmid according to Embodiment 19 in the method for plant transformation according to any one of Embodiments 12 to 14.

Advantageous Effects of Invention

The method plant transformation using the *Agrobacterium* bacterium applying the system of the present invention provides a higher transformation efficiency compared to a (super) ternary vector system using a conventionally known booster vector or a super binary system. In particular, a significant effect is seen in maize.

BRIEF DESCRIPTION OF DRAWINGS

The patent or application file contains at least one color drawing. Copies of this patent or patent application publication with color drawing will be provided by the USPTO upon request and payment of the necessary fee.

DESCRIPTION OF EMBODIMENTS

Figure 1:
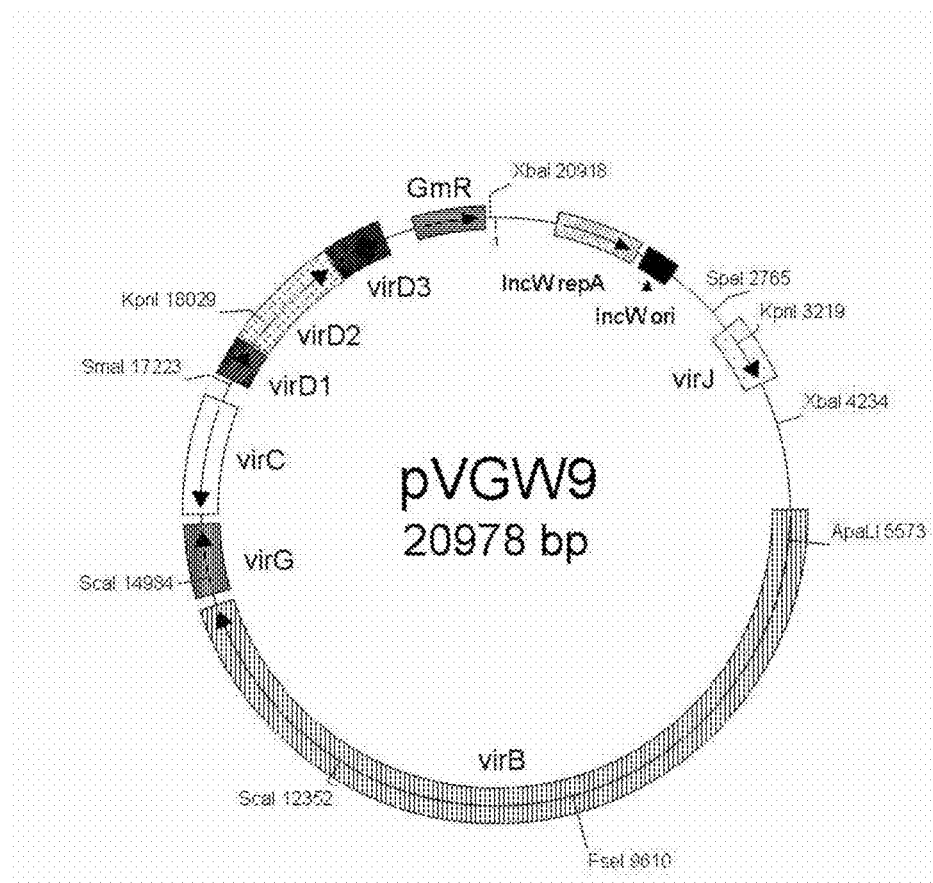
FIG. 1 is a schematic view of the pVGW9 plasmid.
Figure 2:
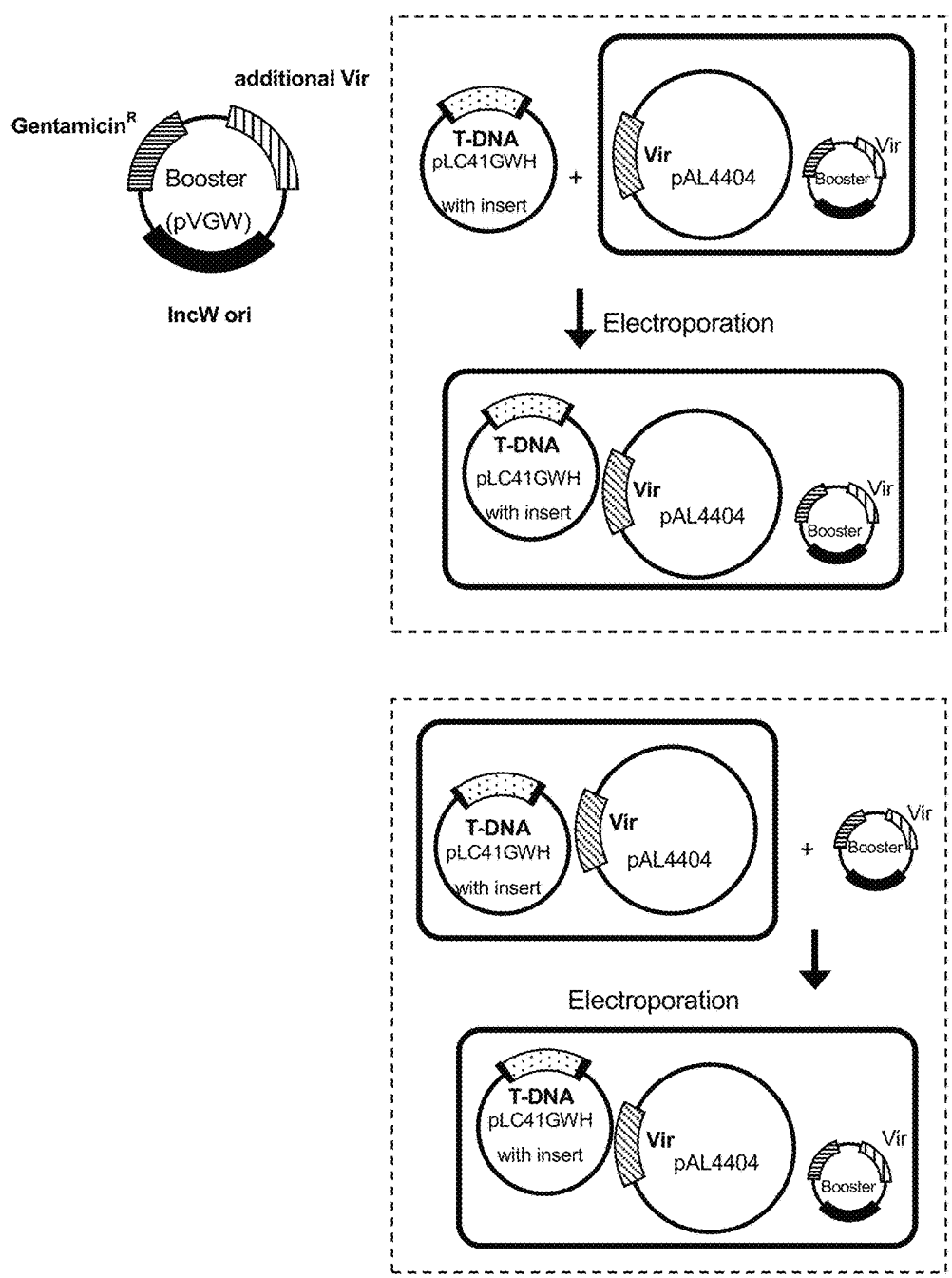
FIG. 2 is a schematic view of a super ternary vector system of the present invention.

I. *Agrobacterium* Bacterium
The present invention relates to the *Agrobacterium* bacterium to be used in plant transformation.

In the present specification, the *Agrobacterium* bacterium is a collective name of those bacterium in the genus *Rhizobium* that have virulence against plants, and it includes those classified as *Agrobacterium tumefaciens*, and *Agrobacterium rhizogenes*. The *Agrobacterium* bacterium of the present invention does not comprise a wild-type Ti plasmid and a wild-type Ri plasmid.

The *Agrobacterium* bacterium of the present invention comprises three types of plasmids described in (1) to (3) below.

(1) a plasmid comprising the following components:
(i) the virB gene, the virC gene, the virD1 gene, the virD2 gene, the virD3 gene, the virG gene and the virJ gene of pTiBo542, and
(ii) an origin of replication;
(2) a disarmed Ti plasmid or a disarmed Ri plasmid of *Agrobacterium* bacterium; and
(3) a plasmid having a T-DNA region consisting of a desired DNA.

Since plasmid vectors of three types, (1) to (3), are used, the system is called a super ternary vector system. In particular, plasmid (1) used as a booster vector is new and has the following features.

(1) Booster Vector

In the present specification, a vector plasmid that can improve the gene introduction efficiency and the transformation efficiency and that can be additionally used in *Agrobacterium* bacterium is called a booster vector. The plasmid (1) having the following components, is used as a booster vector in the present invention. The plasmid (1) comprises (i) the virB gene, the virC gene, the virD1 gene, the virD2 gene, the virD3 gene, the virG gene and the virJ gene of pTiBo542, and (ii) an origin of replication.

(i) virB gene, virC gene, virD1 gene, virD2 gene, virD3 gene, virG gene and virJ gene of pTiBo542

The Ti plasmid is a gigantic plasmid of generally around 200,000 base-pairs contained in the wild-type Agrobacterium, and it comprises T-DNA (transfer DNA) that are introduced into plants, virulence region (vir region), etc. T-DNA is a DNA fragment inserted into the genome of a plant cell by non-homologous end joining, and it comprises the genes for synthesizing growth regulating factors of plants (auxin and cytokinin), and the opine synthetic gene. The vir region is a region for encoding a protein group required for integration of T-DNA into plants, and it comprises the genes, such as the virA gene, the virB gene, the virC gene, the virD1 gene, the virD2 gene, the virD3 gene, the virG gene and the virJ gene.

The vir region of a Ti plasmid contained in "pTiBo542" (Jin et al., 1987), which is a Ti plasmid owned by the highly virulent *Agrobacterium* strain A281, has a particularly high transformation efficiency and it is called a super virulence region (Super-vir region).

The booster vector of the present invention is characterized in that it comprises all of the virB gene, virC gene, virD1 gene, virD2 gene, virD3 gene, virG gene and virJ gene of pTiBo542.

The virB gene is described in detail in Ward et al. (1988) J Biol Chem 263:5804-5814.

For example, it can be prepared by a conventional method from plasmids, such as pSB1 (Komari et al. 1996 Plant J 10:165-174). The DNA sequence of the virB gene corresponds to bases at 3416-12851 in the DNA sequence of Genbank/EMBL Accession No. AB027255 (pSB1). Note that the virB region is an operon consisting of multiple genes, but it will be referred to as the "virB gene" in the present specification.

The virC gene is described in detail in Close et al. (1987). For example, it can be prepared by a conventional method from plasmids, such as pSB1. The DNA sequence of the virC gene corresponds to bases at 163574-164880 in the DNA sequence of Genbank/EMBL Accession No. DQ058764. Note that the virC region is an operon consisting of multiple genes, but it will be referred to as the "virC gene" in the present specification.

The virD gene is composed of the five genes, the virD1 gene, the virD2 gene, the virD3 gene, the virD4 gene and the virD5 gene. The virD gene is described in detail, for example in Ream, W. (2008. Production of a mobile T-DNA by *Agrobacterium tumefaciens*. In *Agrobacterium*, T. Tzfira and V. Citovsky, eds (New York: Springer Science+Business Media, LLC), pp. 280-313). Of the existing virD genes, the booster vector of the present invention comprises the virD1 gene, the virD2 gene, the virD3 gene. The virD1 gene, virD2 gene and virD3 gene respectively correspond to bases at 165149-165592, at 165626-166900 and at 166920-167558 in the DNA sequence of Genbank/EMBL Accession No. DQ058764.

The virG is a transcriptional control (activation) factor of the other vir gene group, such as virB or virE (Winans et al. 1986 Proc. Natl. Acad. Sci. USA 83: 8278-8282). The DNA sequence of the virG gene corresponds to bases at 162660-163463 in the DNA sequence of Genbank/EMBL Accession No. DQ058764.

The virJ gene is described in detail in Pantoja et al. (2002). For example, it can be prepared by a conventional method from plasmids, such as pTiBo542. The DNAsequence of virJ corresponds to bases at 150873-151616 in the Genbank/EMBL Accession No. DQ058764.

Also available for use are genes consisting of DNA that comprises a DNAsequence that hybridizes to the sequence specified above or the complementary sequence of the abover sequence under a stringent condition, and that has the function of each sequence. Also available for use are genes consisting of DNAs that comprise DNA sequences having 80%, 85%, 90%, 95%, 96%, 97%, 98%, 99% identity to the above DNAsequence and that have functions of those sequences. However, they are not limited to these genes.

In the present specification, the term "under a stringent condition" means to hybridize under moderately or highly stringent conditions. To be more specific, moderately stringent conditions can be readily determined by those having ordinary skill in the art based on the length of DNA, for example. The basic conditions are set forth in Sambrook et al., Molecular Cloning: A Laboratory Manual, 3rd ed., Chapter 6, Cold Spring Harbor Laboratory Press, 2001, and includes a prewashing solution of 5×SSC, 0.5% SDS, 1.0 mM EDTA (pH 8.0), a hybridization condition at about 42° C., about 50% formamide, 2× to 6×SSC, preferably 5× to 6×SSC, 0.5% SDS (or other similar hybridization solution such as Stark's solution at about 42° C. in a formamide of about 50%), and it includes about 50° C. to 68° C., 0.1×, to 6×SSC, 0.1% SDS washing condition. Preferably, a moderately stringent condition includes a hybridization condition (and a washing condition) of about 50° C., 6×SSC, 0.5% SDS. The moderately stringent conditions can also be determined readily by a person skilled in the art based on, for example, the length of DNA.

Generally, these conditions include hybridization (e.g. hybridization containing SDS of about 0.5%, about 65° C., 6×SSC to 0.2×SSC, preferably 6×SSC, more preferably 2×SSC, more preferably 0.2×SSC, or 0.1 SSC) and/or washing at higher temperatures and/or lower salt concentration than a moderately stringent condition, and it is accompanied for example with a hybridization condition described above and washing at 65° C. to 68° C., 0.2× to 0.1×SSC, 0.1% SDS. In a buffer for hybridization and washing, SSC (1×SSC is 0.15M NaCl and 15 mM sodium citrate) can be replaced by SSPE (1×SSPE is 0.15M NaCl, 10 mM $NaH_2PO_4$, and 1.25 mM EDTA, pH 7.4), and washing is performed for about 15 minutes to 1 hour after hybridization completes.

In addition, a commercially available hybridization kit that does not use a radioactive substance as a probe can be used. Specifically speaking, hybridization using ECL direct labeling & detection system (Amersham) can be performed. For example, stringent hybridization is performed by adding a blocking reagent to the hybridization buffer in the kit until it reaches 5% (w/v), and NaCl until it reaches 0.5 M, and hybridization is performed at 42° C. for 4 h., and washing is performed in 0.4% SDS, 0.5×SSC twice at 55° C. for 20 min., and once in 2×SSC at room temperature for 5 min.

The percent identity of two DNA sequences can be determined by visual inspection and mathematical calculation, or more preferably, the comparison is made by comparing sequence information using a computer program. An exemplary, preferred computer program is the Genetics Computer Group (GCG; Madison, Wis.) Wisconsin package version 10.0 program, "GAP" (Devereux et al., 1984, Nucl. Acids Res. 12: 387). This "GAP" program can be used to compare not only two DNA sequences but also two amino acid sequences or a DNA sequence and an amino acid sequence. The preferred default parameters for the "GAP" program include: (1) The GCG implementation of a unary comparison matrix (containing a value of 1 for identities and 0 for non-identities) for nucleotides, and the weighted amino acid comparison matrix of Gribskov and Burgess, Nucl. Acids Res. 14: 6745, 1986 as described by Schwartz and Dayhoff, eds., "Atlas of Polypeptide Sequence and Structure", National Biomedical Research Foundation, pp. 353-358, 1979; or other comparable comparison matrices; (2) a penalty of 30 for each gap and an additional penalty of 1 for each symbol in each gap for amino acid sequences, or a penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used, such as, for example, the BLASTN program version 2.2.7, available for use via the National Library of Medicine website (www.ncbi.nlm-.nih.gov/blast/b12seq/bls.html), or the UW-BLAST 2.0 algorithm. The standard default parameter setting of UW-BLAST 2.0 can be seen in the following website (blast.wus-tl.edu). In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, Analysis of compositionally biased regions in sequence databases, Methods Enzymol. 266: 544-71) or segments consisting of short-periodicity internal repeats (as determined by the XNU program of Clayerie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

In the booster vector of the present invention, the positions of the virB gene, the virC gene, the virD1 gene, the virD2 gene, the virD3 gene, the virG gene and the virJ gene of pTiBo542 on the vector are not particularly limited. For example, the vir region fragments (FIG. 7) derived from pTiBo542 comprising all of these genes can be preferably used.

(ii) Origin of Replication

The booster vector of the present invention ((1) plasmid) comprises an origin of replication that allows replication in *E. coli* and the *Agrobacterium* bacterium. For example, an origin of replication selected as necessary from an origin of replication of the IncW incompatibility group, an origin of replication of the IncP incompatibility group, an origin of replication of the IncQ incompatibility group and an origin of replication of the pVS1 incompatibity group may be used without being limited thereby.

The origin of replication is preferably an origin of replication of the IncW incompatibility group, more preferably an origin of replication of IncW. The molecular biological features of the origin of replication of the IncW plasmid is described in detail in Okumura and Kado (1992 Mol Gen Genet 235: 55-63), and it corresponds to bases at 2170-2552 in the Genbank/EMBL Accession No. U30471 (full length 5500 bp). The origin of replication of the IncW plasmid can be prepared by a conventional method from IncW plasmids, such as pTOK47 (Jin et al. 1987).

In addition, it is preferable to comprise a coding region of the RepA protein (initiator) to make the origin of replication of a IncW plasmid function. The DNA sequence of the repA gene is not particularly limited as long as it is a sequence that functions as the repA gene necessary for the replication of IncW plasmid. The molecular biological features of repA necessary for the IncW plasmid is described in detail in Okumura and Kado (1992 Mol Gen Genet 235: 55-63), and it corresponds to bases at 1108-2079 in the Genbank/EMBL Accession No. U30471 (full length 5500 bp).

repA necessary for replicating the IncW plasmid can be prepared by a conventional method from a IncW plasmid, such as pTOK47 (Jin et al. 1987).

(iii) Other Components

The booster vector ((1) plasmid) of the present invention can further comprise other genes in the vir region of pTiBo542, for example, the virE gene, virD4 gene or virD5 gene.

The virE gene is described in detail in Citovsky et al. (1988). For example, it can be prepared by a conventional method from plasmids, such as pTiBo542. The DNA sequence of virE corresponds to bases at 172574-176510 in the DNA sequence in the Genbank/EMBL Accession No. DQ058764. Note that the virE region is an operon composed of multiple genes, but it is referred to as the "virE gene" in the present specification.

The virD4 gene is described in detail in Christie (2004). For example, it can be prepared by a conventional method from plasmids, such as pTiBo542. The DNA sequence of virD4 corresponds to bases at 167555-169513 in the DNA sequence of Genbank/EMBL Accession No. DQ058764.

The virD5 gene is described in detail in Vergunst et al. (2005). For example, it can be prepared by a conventional method from plasmids, such as pTiBo542. The DNAsequence of virD5 corresponds to bases at 169614-172124 in the DNA sequence of Genbank/EMBL Accession No. DQ058764.

The booster vector of the present invention may further comprise a drug selectable marker gene. The drug selectable marker gene can use a publicly known gene, without being particularly limited thereto. It should preferably be a drug selectable marker gene that is not a part of the Ti plasmid and a plasmid having a T-DNA region (binary vector). As a specific example of a drug selectable marker gene, it is preferable to use a gentamycin resistance gene, without being limited thereby at all. A kanamycin resistance gene, an ampicillin resistance gene, a spectinomycin resistance gene, a tetracycline resistance gene, a hygromycin resistance gene and various other drug selectable marker genes can be preferably used according to the given purpose. The type of the drug selectable marker gene on the booster vector and the binary vector of the present invention can be readily modified by methods such as in fusion PCR.

The full length of the booster vector in the present invention is not limited, but it is preferably 10 kb to 30 kb, and more preferably 15 kb to 25 kb.

(iv) pVGW9

One booster vector of the present invention that satisfies the above condition is pVGW9. pVGW9 has a DNA sequence of SEQ ID NO: 1 attached to the present specification, and has a full length of 20978 base pairs.

FIG. 1 shows the schematic diagram of pVGW9. Each component occupies the following position in the DNA sequence of SEQ ID NO: 1.

Origin of replication: Bases at 9-2758 in SEQ ID NO: 1
virJ gene: Bases at 3003-3746 in SEQ ID NO: 1
virB gene: Bases at 5223-14658 in SEQ ID NO: 1
virG gene: Bases at 14790-15593 in SEQ ID NO: 1
virC gene: Bases at 15704-17010 in SEQ ID NO: 1
virD1 gene: Bases at 17279-17722 in SEQ ID NO: 1
virD2 gene: Bases at 17756-19030 in SEQ ID NO: 1
virD3 gene: Bases at 19050-19688 in SEQ ID NO: 1

(2) Disarmed Ti Plasmid or a Disarmed Ri Plasmid of *Agrobacterium* Bacterium

The *Agrobacterium* bacterium of the present invention further comprises a disarmed Ti plasmid or a disarmed Ri plasmid of the *Agrobacterium* bacterium (they may be collectively referred to as the "Ti plasmid" in the present specification).

The Ri plasmid is a plasmid specifically contained in the *Agrobacterium rhizogenes* among bacterium of the genus *Agrobacterium*. Similar to the Ti plasmid, it is a gigantic plasmid of around 200,000 base pairs, and it comprises T-DNA (transfer DNA) to be introduced into the plant, and the virulence region (vir region).

Note that the origin of replication of a disarmed Ti plasmid or a disarmed Ri plasmid of the *Agrobacterium* bacterium belongs to a different incompatibility group as IncW, IncP, IncQ and pVS1.

The "disarmed Ti plasmid or the disarmed Ri plasmid" is a plasmid produced by removing the T-DNA region from a wild-type Ti plasmid or a wild-type Ri plasmid. Preferably, the disarmed plasmid of *Agrobacterium* bacterium is a disarmed Ti plasmid.

It is possible to use pAL4404 described in Hoekema et al. (1983) as a disarmed Ti plasmid. It is possible to use pRiB278b described in Jouanin et al. (1987) as a disarmed Ri plasmid.

Alternatively, it is also possible to use a publicly known *Agrobacterium* strain that originally has disarmed Ti plasmid. The *Agrobacterium* bacterium of the present invention preferably does not comprise a disarmed pTiBo542. It is possible to use, for example, LBA4404, GV3850, GV3TillSE, C58-Z707, GV3101::pMP90, GV3101::pMP90RK, GV2260, or NTI (pKPSF2) without being limited thereby.

(3) Binary Vector (Plasmid Having a T-DNA Region Consisting of a Desired DNA)

The *Agrobacterium* bacterium of the present invention comprises a plasmid having T-DNA consisting of the desired DNA. This plasmid can be replicated in both *Agrobacterium* and *E. coli*, and it is called a binary vector. As a binary vector, those which are publicly known can appropriately be used. Specific examples include pBin19, pBI121, pIG121, pIG121Hm, pLC41, vectors of pGreen series, vectors of pCLEAN-G series, vectors of pPZP series, vectors of pCAMBIA series, pOREO1, pGWB or the like.

The DNA to be inserted into the T-DNA region of the present invention is not particularly limited. For example, it is possible to use any DNA, such as a genome DNA fragment, or a cDNA fragment. Preferably, a genome DNA, more preferably, a genome DNA from a plant can be used. A preferable, non-limiting size of a DNA fragment is 0.1 kb-100 kb, and more preferably 1 kb-40 kb.

When inserting a large fragment of T-DNA to a binary vector, it is preferable to use an origin of replication of an Ri plasmid (Hamilton, C. M., Frary, A., Lewis, C., and Tanksley, S. D. (1996). Stable transfer of intact high molecular weight DNA into plant chromosomes. Proc Natl Acad Sci USA 93, 9975-9979).

In the present invention, each of plasmids (1) to (3) has a replication mechanism that can mutually coexist with each other. When the binary vector and the booster vector are in the same incompatibility group, they cannot coexist in an *Agrobacterium*. Hence, the origins of replication of these vectors need to be in different incompatibility groups from each other. For example, IncW, IncP, IncQ and pVS1, each belongs to a different incompatibility group from the others. By "each of plasmids of (1) to (3) has a replication mechanism that enables mutual coexistence with each other," it is meant that each of the three types of plasmids (1) to (3) belongs to a different incompatibility group from the others, for example, to IncW, IncP, IncQ, which differ mutually. This requirement cannot be satisfied if at least two out of the three types of plasmids belong to the same group.

Embodiments of *Agrobacterium* Bacterium of the Present Invention

The order and the method for introducing the three types of plasmids (1) to (3) into the *Agrobacterium* bacterium are not particularly limited.

For example, it is possible to use a publicly known *Agrobacterium* strain that originally has disarmed Ti plasmid (corresponding to plasmid (2)). For example, Strains of LBA4404 (Hoekema et al., 1983), GV3850 (Zambryski et al., 1983), GV3TillSE (Fraley et al., 1985), C58-Z707 (Hepburn et al., 1985), GV3101::pMP90 (Koncz and Schell, 1986), GV3101::pMP90RK (Koncz and Schell, 1986), GV2260 (McBride and Summerfelt, 1990), or NTI (pKPSF2) (Palanichelvam et al., 2000) can be used, without any limitation. A booster vector ((1) plasmid) and a binary vector ((3) plasmid) may be introduced into these *Agrobacterium* strains. A booster vector and a binary vector can be introduced by a conventionally known method, such as electroporation, triparental mating, and freezing-thaw method. The order of introducing the booster vector and the binary vector is not particularly limited. The two can be introduced at the same time.

In an embodiment of the present invention, the *Agrobacterium* bacterium is produced by introducing the plasmid (1) and the plasmid (3) into the *Agrobacterium* bacterium selected from the group consisting of LBA4404, GV3850, GV3TillSE, C58-Z707, GV3101::pMP90, GV3101::pMP90RK, GV2260, and NTI (pKPSF2).

The present invention also includes an embodiment of *Agrobacterium* bacterium comprising plasmids described in (1) to (2) shown below:
(1) a plasmid comprising the following components:
   (i) the virB gene, the virC gene, the virD1 gene, the virD2 gene, the virD3 gene, the virG gene and the virJ gene of pTiBo542, and
   (ii) an origin of replication; and
(2) a disarmed Ti plasmid or a disarmed Ri plasmid of *Agrobacterium* bacterium;

wherein each of the plasmid (1) and the plasmid (2) has a replication mechanism that enables a mutual coexistence with each other.

The *Agrobacterium* bacterium comprising the plasmids (1) and (2) may further incorporate a binary vector that has a T-DNA region to which a desired DNA is inserted (3), and the *Agrobacterium* bacterium is applicable for a wide variety of use.

II. Plant Transformation

The present invention relates to a method for plant transformation using the *Agrobacterium* bacterium of the present invention, and a method for introducing genes into plants. The method of the present invention comprises contacting the *Agrobacterium* bacterium of the present invention with a plant cell.

The present invention also includes an embodiment of introducing the plasmid (3) having a T-DNA region consisting of a desired DNA to the *Agrobacterium* bacterium comprising plasmids described in (1) to (2) shown below:
(1) a plasmid comprising the following components:
   (i) the virB gene, the virC gene, the virD1 gene, the virD2 gene, the virD3 gene, the virG gene and the via gene of pTiBo542, and
   (ii) an origin of replication; and
(2) a disarmed Ti plasmid or a disarmed Ri plasmid of *Agrobacterium* bacterium;

wherein each of the plasmid (1) and the plasmid (2) has a replication mechanism that enables a mutual coexistence with each other. and
   contacting the *Agrobacterium* bacterium with a plant cell.

The plant to be subjected to transformation method of the present invention is not particularly limited, but it is preferably an angiosperm, which may be a monocotyledon or a dicotyledon. The transformation can preferably be used for maize, rice or tomato as described in the Examples of the present specification without being limited thereto.

A use of the *Agrobacterium* bacterium of the present invention in a publicly known transformation method via *Agrobacterium* can greatly improve a transformation efficiency.

III. Kit

The present invention further relates to a kit for use in a method for transforming a plant cells by *Agrobacterium*. In an embodiment of the present invention, the kit includes the *Agrobacterium* bacterium of the present invention.

The present invention further relates to a kit for use in a method for transforming plant cells by *Agrobacterium*. In one embodiment of the present invention, the kit comprises a combination of plasmids of (1) to (3) shown below:
(1) a plasmid comprising the following components:
   (i) the virB gene, the virC gene, the virD1 gene, the virD2 gene, the virD3 gene, the virG gene and the virJ gene of pTiBo542, and
   (ii) an origin of replication;

(2) a disarmed Ti plasmid or a disarmed Ri plasmid of *Agrobacterium* bacterium; and
(3) a plasmid having a T-DNA region consisting of a desired DNA;

wherein each of the plasmids of (1) to (3) has a replication mechanism that enables a mutual coexistence with each other.

In another embodiment of the present invention, the kit comprises a combination of plasmids of (1) and (3) shown below:
(1) a plasmid comprising the following components:
   (i) the virB gene, the virC gene, the virD1 gene, the virD2 gene, the virD3 gene, the virG gene and the virJ gene of pTiBo542, and
   (ii) an origin of replication; and
(3) a plasmid having a T-DNA region consisting of a desired DNA;

wherein each of the plasmids of (1) and (3) has a replication mechanism that enables a mutual coexistence with each other. In the embodiment, the kit may further comprise *Agrobacterium* bacterium selected from LBA4404, GV3850, GV3TillSE, C58-Z707, GV3101::pMP90, GV3101::pMP90RK, GV2260, and NTI (pKPSF2).

IV. Plasmid

The present invention further relates to a plasmid (1) comprising the following components:
   (i) the virB gene, the virC gene, the virD1 gene, the virD2 gene, the virD3 gene, the virG gene and the virJ gene of pTiBo542, and
   (ii) an origin of replication. The plasmid of the present invention is preferably the pVGW9 plasmid having a DNA sequence of SEQ ID NO: 1.

The present invention also relates to the use of the plasmid of the present invention in a plant transformation method according to any one of Embodiments 12-14.

V. Vector System for Transformation of Plant Cells

The present invention further provides a vector system for transforming plant cells (super ternary vector system) that uses a combination of the above three types of plasmids (1) to (3).

The conventionally known super binary vector mentioned above is a hybrid vector obtained by homologous recombination between an acceptor vector that incorporates a KpnI fragment (a part of the virD1 gene, the virB gene, the virC gene and the virG gene) of 14.8 kb and a shuttle vector carrying the desired T-DNA cloned in *E. coli*. Accordingly, since an acceptor vectors is required to be introduced into *Agrobacterium* in advance, preparation becomes quite burdensome in a test of many types of *Agrobacterium* strains. Furthermore, Patent Document WO 2007/148819 A1 reports that the hybrid vector in the *Agrobacterium* was unstable when a large T-DNA of 30 kb to 40 kb was tried to be inserted by homologous recombination. This instability is considered to be due to the fact that the origin of replication of the shuttle vector is the multicopy ColE1.

In comparison, it is possible to use the super ternary vector system of the present invention in plant transformation by previously introducing a booster vector into the *Agrobacterium* strain that holds a disarmed Ti plasmid, then introducing a binary plasmid carrying a T-DNA that incorporates a desired gene into that *Agrobacterium* strain by electroporation. In other words, a super ternary vector system may be readily constructed just by using electroporation and introducing the booster vector of the present invention into a binary vector strain used widely in various plants, and this enables transformed plants to be obtained at an extremely high efficiency.

EXAMPLES

The present invention is explained in detail below based on the Examples, but the present invention is not limited to these Examples. A person skilled in the art would easily modify/change the present invention based on the description in the present specification, and such modification/change is also within the technical scope of the present invention.

Example 1

Construction of a Super Ternary Vector System

Figure 3:
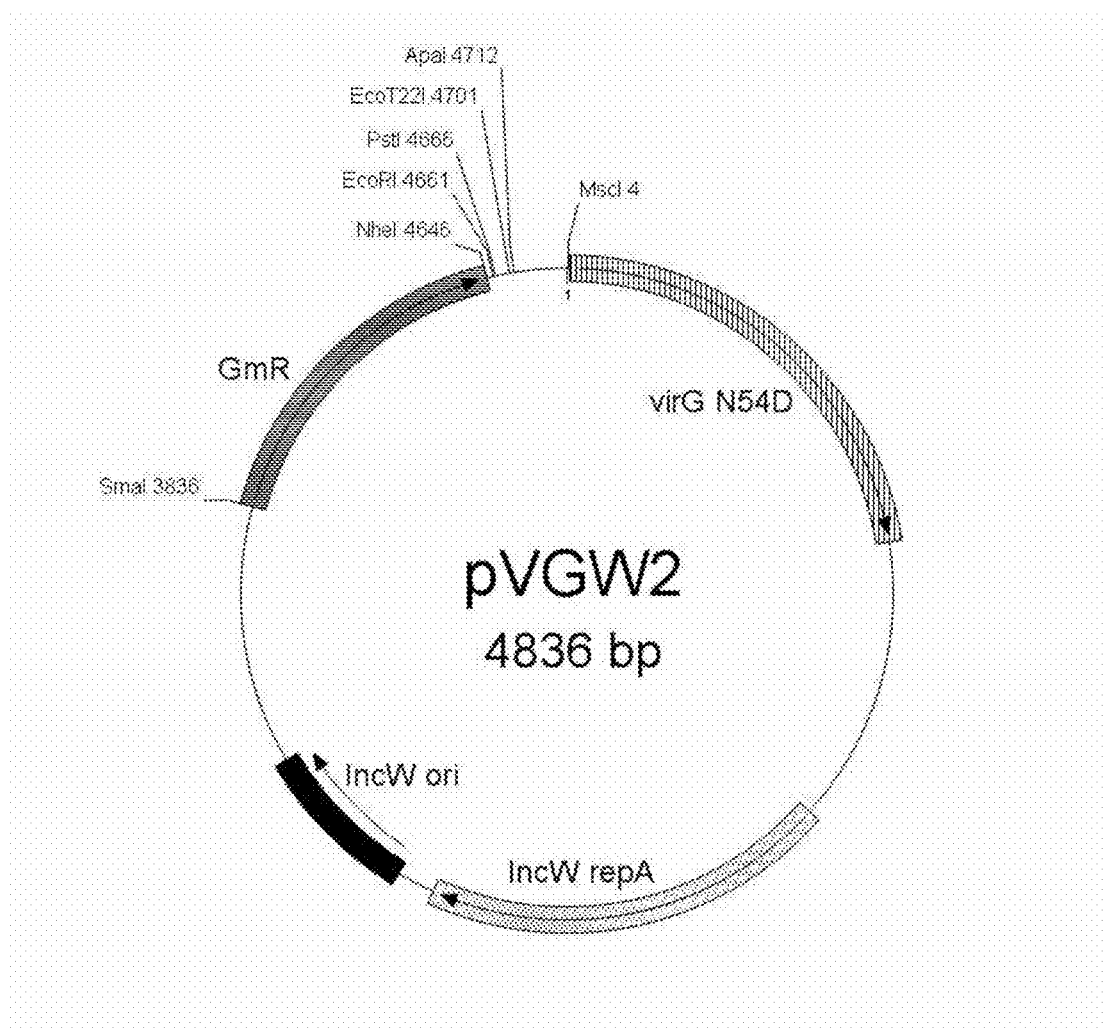
FIG. 3 is a schematic view of the pVGW2 plasmid.

The present Examples describe constructing a vector system (super ternary vector system) using three types of plasmids of the present invention.

pTOK47 comprises both the IncW ori and the pBR322 ori, and its full length is 28 kb (Jin et al., 1987). Furthermore, the full length of pAL154 (Amoah et al., 2001) is 24 kb. These booster vectors are large plasmids that comprise many sequences that are unnecessary for maintaining replication in the *Agrobacterium*. The vector to be used as a booster vector in the super ternary vector system should be a shuttle vector that is desirably smaller in size, readily incorporates the vir region fragment, and can be cloned into *E. coli*. Patent Document WO2007/148819 A1 discloses a vector pVGW2 that suits these requirements. pVGW2 comprises both an IncW ori and a pBR322 ori, and it carries a gentamycin resistance gene (FIG. 3). In the present Examples, a booster vector having a virulence region of pTiBo542 was constructed based on pVGW2.

Figure 4:
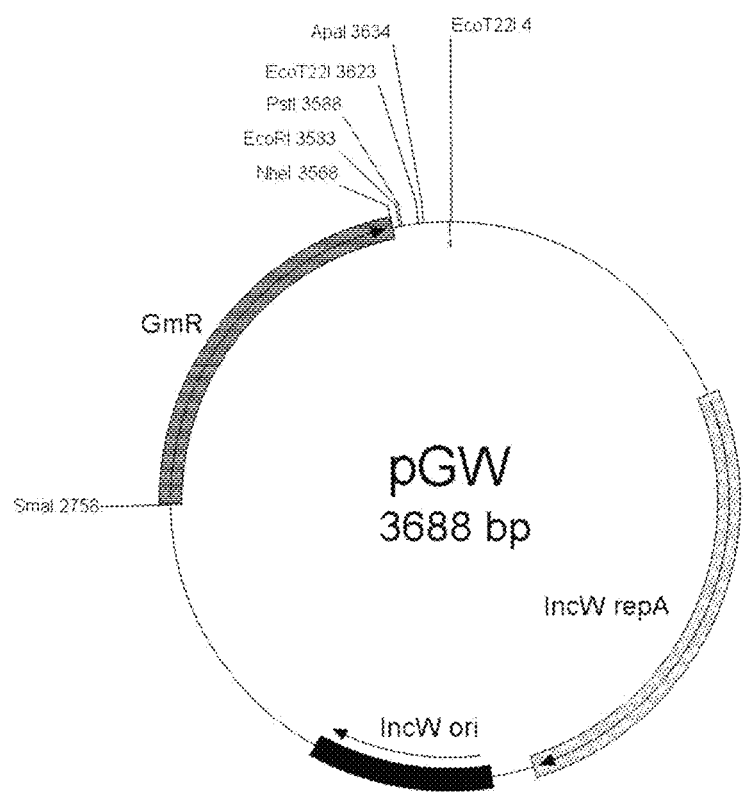
FIG. 4 is a schematic view of the pGW plasmid.

At first, pVGW2 was used as a template to perform PCR with a primer set of pSa5'EcT22I (5'-AAA ATG CAT GGC ATG TTT AAC AGA ATC TG-3') (SEQ ID NO: 2) and M13 (−20) Fw (5'-GTA AAA CGA CGG CCA G-3') (SEQ ID NO: 3), and the obtained fragment was subjected to self-ligation to construct a new cloning vector "pGW" (FIG. 4). "PrimeSTAR Max" (TaKaRa) with a high fidelity was used as the PCR reagent. This reagent was used in all PCRs related to the constructions.

Preparation of Booster Vector pVGW7

Figure 5:
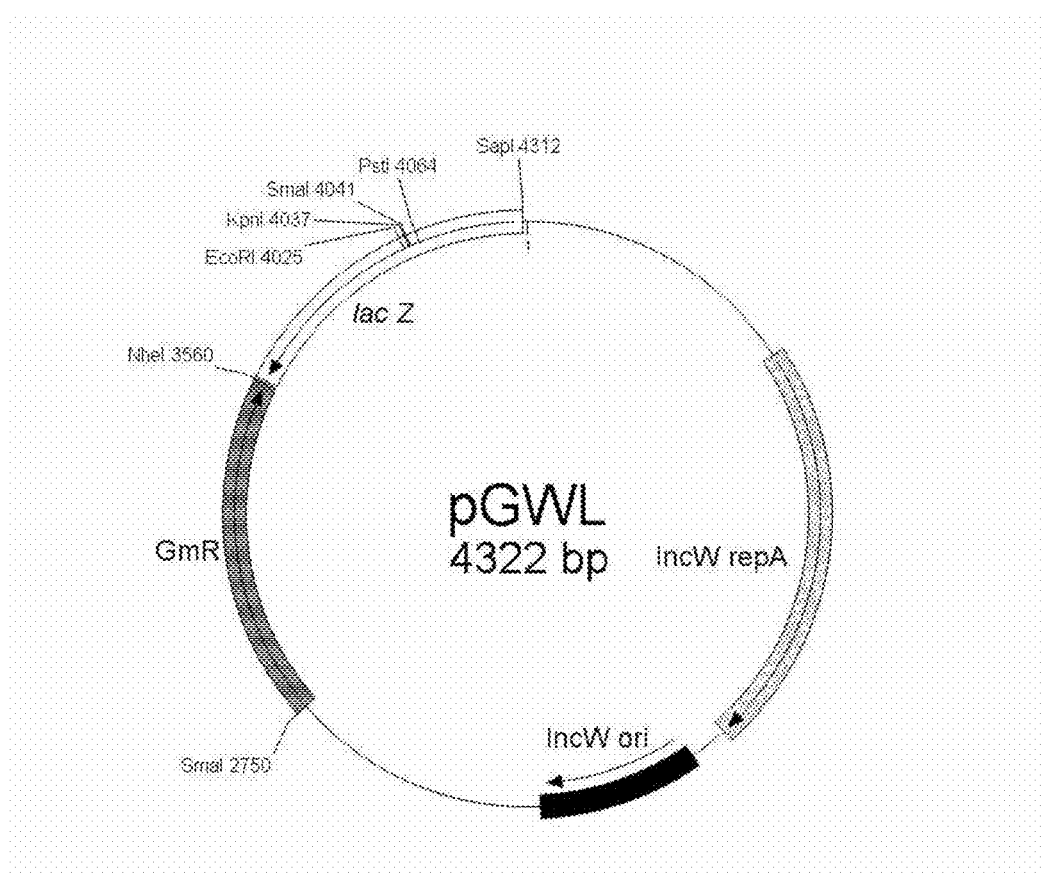
FIG. 5 is a schematic view of the pGWL plasmid.
Figure 6:
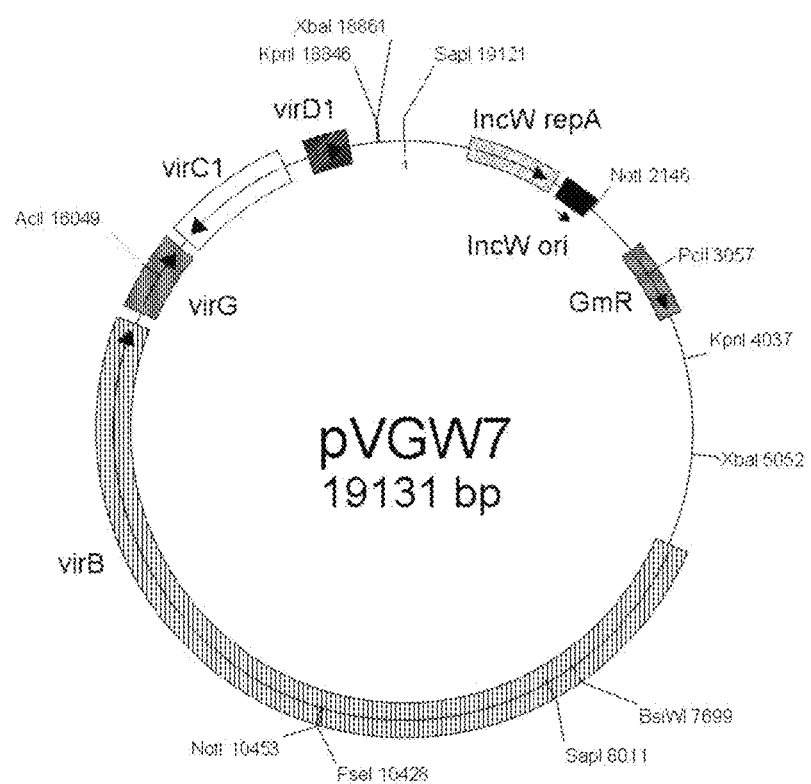
FIG. 6 is a schematic view of the pVGW7 plasmid.
Figure 7:
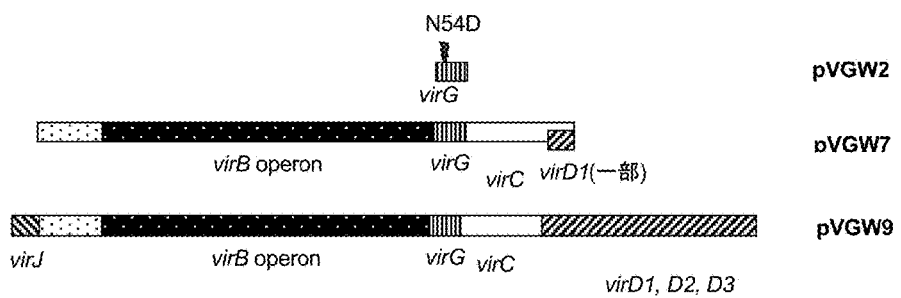
FIG. 7 is a schematic view of the vir region derived from pTiBo542 used by being added to a booster vector.

A booster vector pVGW7 that comprises a KpnI fragment of 14.8 Kb retained in pTOK47 and pAL154 as a vir gene group was prepared. Firstly, a lactose operon of pUC19 was incorporated into pGW to improve the work efficiency during cloning. A lactose operon fragment obtained by digesting pUC19 with SapI+AatII was inserted into the NsiI-NheI site in pGW to obtain a new cloning vector "pGWL" (FIG. 5). A fragment obtained by digesting pSB1 with KpnI was inserted into the KpnI site of pGWL to obtain pVGW7 (FIG. 6, FIG. 7).

Preparation of Booster Vector pVGW9

A test was performed to confirm whether a further expansion of the region of vir genes derived from pTiBo542 to be inserted into a booster plasmid would further improve the transformation ability. PCR was performed using a primer phosphorylated in advance, pTiBo542:150641Fw (5'-aaa aac tag tca gag cca ccc cat cag gaa tat cgc cca ttc cgt cat cag cgt ggt gac-3') (SEQ ID NO: 4) and delD2-3'Rv (5'-tcc aaa gat egg ccc at gat gcg act gta acg ctg cag ata ac-3') (SEQ ID NO: 5) with pTiBo542 as the template, and the amplified product was ligated to both ends of a pGW vector that has been opened by SmaI and dephosphorylated. As a result, the target construct pVGW9 (FIG. 1, FIG. 7) comprising all regions of the virB, virC, virD1, D2, D3, virG and virJ genes was obtained. The DNA sequence of pVGW9 is shown as SEQ ID NO: 1 in the sequence lists.

Preparation of pLC41GWH-IG

Figure 8:
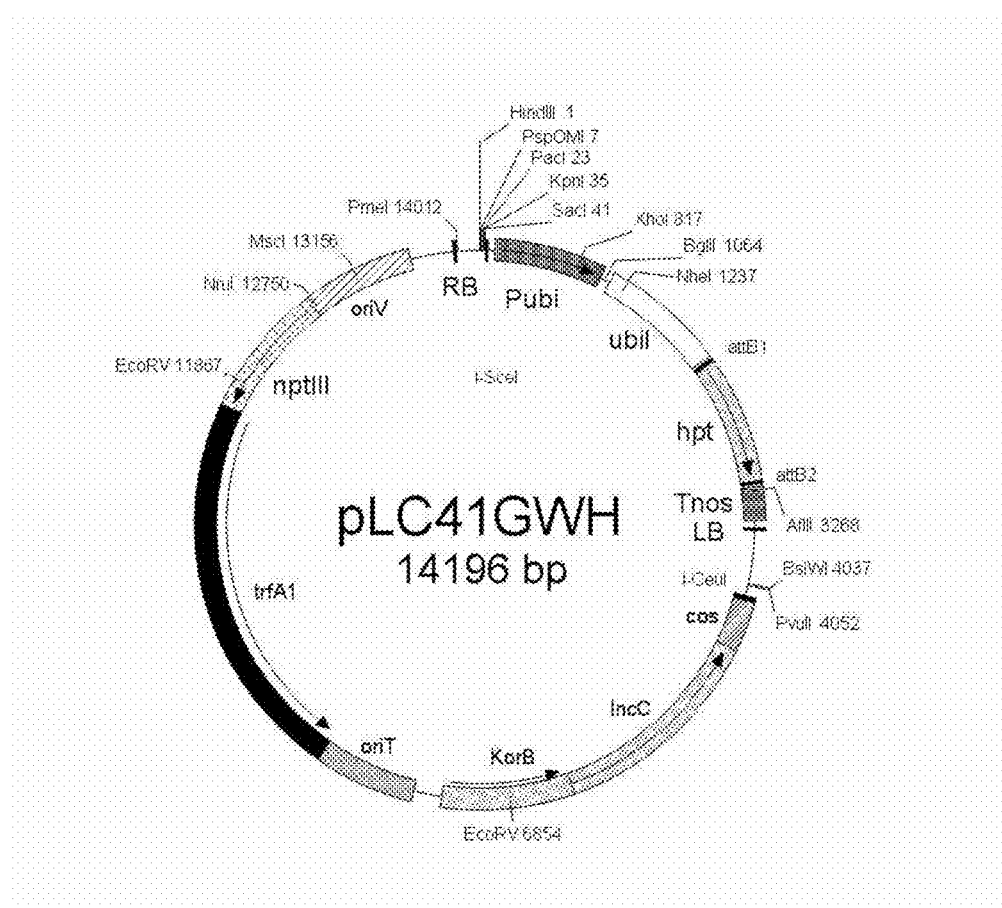
FIG. 8 is a schematic view of the pLC41GWH plasmid.
Figure 9:
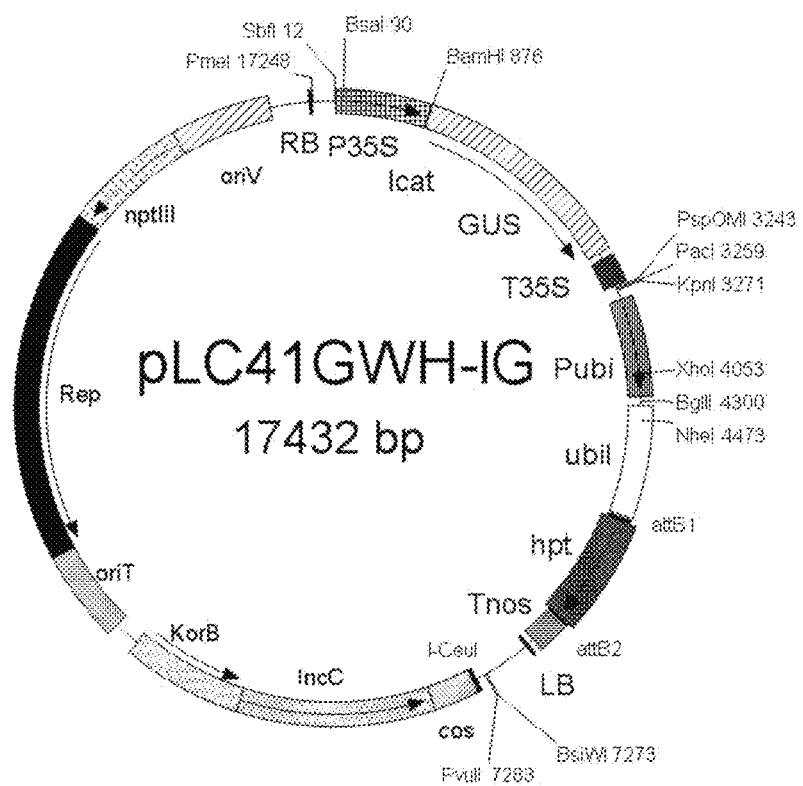
FIG. 9 is a schematic view of the pLC41GWH-IG plasmid.

The cosmid vector pLCleo (otherwise known as pLC41GWH) described in Patent Document WO 2007/148819 A1, is an IncP plasmid and has the oriV origin of replication (FIG. 8). oriV functions in both the *E. coli* and *Agrobacterium*. In addition, it has a hygromycin resistance gene regulated by a promoter accompanying a first intron of a ubiquitin gene of maize in the T-DNA region. To insert a GUS gene which is mediated by a first intron of castor bean catalase gene and is regulated by the 35S promoter of CaMV (P35S:Icat:GUS:T35S) to the multiple cloning site (MCS) of pLC41GWH, pLC41GWH and pSB34 (Hiei and Komari, 2006) were digested with HindIII. The digested sample was subjected to electrophoresis with 0.7% SeaKem GTG agarose, and the target band was extracted from the gel and purified using QIAEX II (QIAGEN). The vector fragment and the fragment to insert were ligated (16° C., one night), and the reaction solution was precipitated in ethanol and re-dissolved by MilliQ water, then it was introduced into *E. coli* GeneHogs (Invitrogen) by electroporation. Then it was cultured on a LB agar medium containing an antibiotic, kanamycin (50 μg/ml), and the obtained colony was purified to produce plasmids. The DNA sequences of these clones were determined, and one of those which was confirmed to have the desired insert was named as binary vectors pLC41GWH-IG (FIG. 9).

Preparation of Binary Vector Strains and Super Ternary Vector Strains pLC41GWH-IG was introduced into the *Agrobacterium* strains, LBA4404, GV2260, GV3850, by electroporation, then they were cultured on an AB agar media containing antibiotics kanamycin (50 μg/ml) and hygromycin (50 μg/ml) to obtain three types of binary vector strains. The booster vector pVGW7 was introduced into LBA4404 (pLC41GWH-IG) by electropolation, then it was cultured on an AB agar medium containing kanamycin (50 μg/ml), hygromycin (50 μg/ml) and gentamicin (30 μg/ml) to obtain a super ternary vector strain LBA4404 (pLC41GWH-IG/pVGW7). Further, the booster vector pVGW9 was introduced into each of the LBA4404 (pLC41GWH-IG), GV2260 (pLC41GWH-IG), GV3850 (pLC41GWH-IG) strains by electropolation, and they were cultured on an AB agar medium containing kanamycin (50 μg/ml), hygromycin (50 μg/ml) and gentamicin (30 μg/ml) to obtain super ternary vector strains LBA4404 (pLC41GWH-IG/pVGW9), GV2260 (pLC41GWH-IG/pVGW9), GV3850 (pLC41GWH-IG/pVGW9). Also, a booster vector pVGW9 was introduced into the LBA4404 (pIG121Hm) (Hiei et al., 1994) by electropolation, and it was cultured on an AB agar medium containing kanamycin (50 μg/ml), hygromycin (50 μg/ml) and gentamicin (30 μg/ml) to obtain super ternary vector strain LBA4404 (pIG121Hm/pVGW9).

Example 2

Gene Introduction into Maize A188 by Super Ternary Vector System

In the present Example, a super ternary vector strain LBA4404 prepared in Example 1 was used to introduce genes into maize A188.

Materials and Method

An immature embryo of maize of about 1.2 mm large in length (Variety: A188) was taken out aseptically from a greenhouse cultured plant, and it was immersed in a liquid media for suspending *Agrobacterium*, LS-inf (Ishida et al., 2007). After heat treatment at 46° C. for 3 min, the immature embryos were washed once in the liquid medium. Then, they were subjected to centrifugation at 20,000 G for 10 min. (4° C.), followed by immersion of the immature embryos in LS-inf medium containing 100 µM of acetosyringone which contains suspension of the strains of LBA4404 (pLC41GWH-IG), GV2260 (pLC41GWH-IG), GV3850 (pLC41GWH-IG) and LBA4404 (pLC41GWH-IG/pVGW9), GV2260 (pLC41GWH-IG/pVGW9), GV3850 (pLC41GWH-IG/pVGW9) at a concentration of about $1\times10^9$ cfu/ml, after which the immature embryos were placed on the cocultivation medium LS-AS (Ishida et al., 2007). The culture plates were cultured at 25° C., under dark for 3 days, then the GUS activity of the immature embryo was investigated by the treatment of 5-bromo-4-chloro-3-indolyl-β-D-glucuronide (X-Glue).

Result and Discussion

Figure 10:
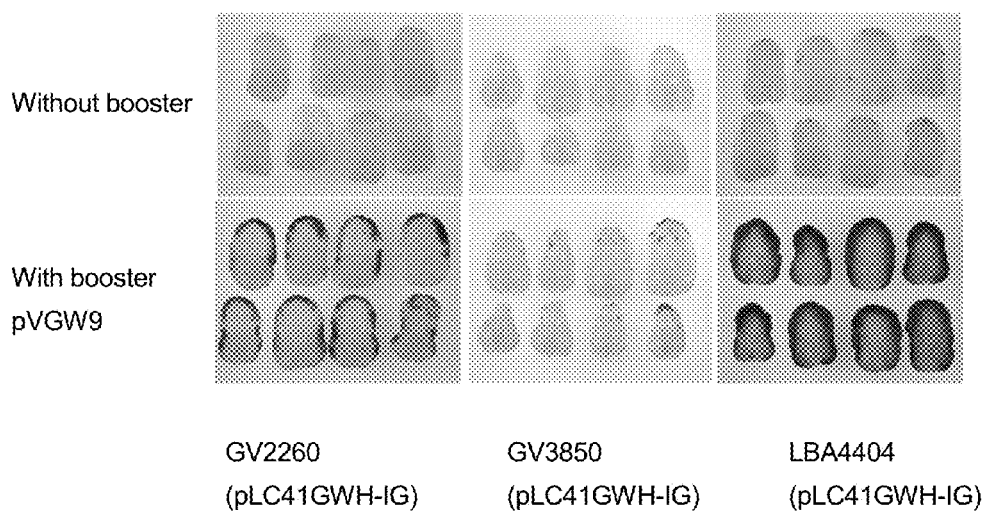
FIG. 10 shows the result of introducing genes to maize A188 by a super ternary vector system.

Various strains were inoculated to immature embryos of A188, and transient expression of GUS gene was observed after 3 days of cocultivation. Among control strains, LBA4404 (pLC41GWH-IG), GV2260 (pLC41GWH-IG) and GV3850 (pLC41GWH-IG), small GUS activity was recognized only in the immature embryos that inoculated with LBA4404 (pLC41GWH-IG). There was almost no gene introduction for GV2260 (pLC41GWH-IG) and GV3850 (pLC41GWH-IG) (FIG. 10).

On the other hand, expression of GUS gene on the scutellum of immature embryo was observed in all experiments using the super ternary vector strains that incorporated the booster vector pVGW9. In particular, frequent GUS expression was observed in the immature embryos which were inoculated with LBA4404 (pLC41GWH-IG/pVGW9) (FIG. 10).

Example 3

Transformation of Maize A188 by Super Ternary Vector Systems

Transformation of maize A188 was performed in the present Example by using the super ternary vector strain LBA4404 which was prepared in Example 1.

Materials and Method

Immature embryos of maize of about 1.2 mm in length (Variety: A188) were taken out aseptically from plants cultured in a greenhouse, and immersed in a liquid media for suspending *Agrobacterium*, LS-inf (Ishida et al.,2007). After heat treatment at 46° C. for 3 min, the immature embryos were washed once in the liquid medium. Then, they were subjected to centrifuge at 20,000 G for 10 min. (4° C.), followed by immersion of the immature embryos in a LS-inf medium containing 100 µM of acetosyringone which contains suspension of the strain of binary vector system LBA4404 (pLC41GWH-IG), and super vector system LBA4404 (pLC41GWH-IG/pVGW7), super ternary vector system LBA4404 (pLC41GWH-IG/pVGW9), and super binary vector system LBA4404 (pSB134) (Hiei and Komari, 2006), after which the immature embryos were placed on the cocultivation medium LS-AS (Ishida et al., 2007). Components of T-DNA including the promoter and terminator region are the same between pSB134 and pLC41GWH-IG. The culture plates ere cultured at 25° C. for three days under the dark condition. The immature embryos after cocultivation were placed on a selective medium containing hygromycin (Hm) (Ishida et al., 2007) to perform cultivation. Proliferated calluses were cut into small pieces, and placed on the regeneration medium (Ishida et al., 2007) containing Hm, then cultured under the light condition. After two weeks, an investigation was carried out concerning regenerated plants showing resistance to Hm.

Result and Discussion

The result is shown in Table 1.

TABLE 1

Result of Transformation in Maize A188

| Tested *Agrobacterium* strains (tested vectors) | Immature embryo | | | |
|---|---|---|---|---|
| | Inoculated (A) | Produced HygR plant | Regenerated GUS positive plant (B) | Transformation efficiency (B/A: %) |
| a LBA4404 (pSB134) | 50 | 4 | 3 | 6.0 |
| b LBA4404 (pLC41GWH-IG) | 51 | 0 | 0 | 0.0 |
| c LBA4404 (pLC41GWH-IG/pVGW7) | 54 | 4 | 4 | 7.4 |
| d LBA4404 (pLC41GWH-IG/pVGW9) | 50 | 12 | 10 | 20.0 | a: Super binary vector system
b: Binary vector system
c: Super ternary vector system
d: Super ternary vector system (present invention)

Any transformed plants were not obtained from the immature embryo inoculated with the binary vector system LBA4404 (pLC41GWH-IG). In all other vector systems incorporating virB, C, G of pTiBo542, maize transformants with Hm resistance and GUS positive properties were obtained (Table 1).

When the vector systems were compared, between the super binary vector system LBA4404 (pSB134) and the super ternary vector system LBA4404 (pLC41GWH-IG/pVGW7), the latter had a rather high transformation efficiency (Table 1). Patent Document WO2007/148819 A1 reports that the super binary vector system having a KpnI fragment of 14.8 kb has a somewhat higher transformation efficiency than the super ternary vector system pTOK47 having a KpnI fragment of 14.8 kb.

In comparison, the super ternary vector system LBA4404 (pLC41GWH-IG/pVGW9) of the present invention had significantly higher transformation efficiency than other vector systems (Table 1). The super ternary vector system having all of the virB, C, D, G, J genes of pTiBo542 is considered to have higher transformation ability than any conventional vector systems.

Example 4

Transformation of Indica Rice IR64 by the Super Ternary Vector System

In the present Example, transformation of the Indica rice IR64 was performed by using the super ternary vector strain LBA4404 which was prepared in Example 1.

Materials and Method

Immature embryos of Indica rice IR64 of 1.5 mm in length were isolated aseptically, placed on a CCM callus induction medium and cultured at 30° C. under the dark condition for 10 days. Calluses that were proliferated from scutella were further cultured at 30° C. under the light condition for two weeks. The obtained calluses were cut into size of 1-2 mm and cultured for further four days, then they were immersed in the liquid media for suspending *Agrobacterium* (AAM medium) prepared in Example 1 (Hiei and Komari, 2008) containing 100 μM of acetosyringone containing a suspension of strains of LBA4404 (pLC41GWH-IG), LBA4404 (pIG121Hm), GV2260 (pLC41GWH-IG), GV3850 (pLC41GWH-IG) and LBA4404 (pLC41GWH-IG/pVGW9), LBA4404 (pIG121Hm/pVGW9), GV2260 (pLC41GWH-IG/pVGW9), GV3850 (pLC41GWH-IG/pVGW9) at a concentration of about $1 \times 10^9$ cfu/ml, after which it was placed on the coculture medium NB-As (Hiei and Komari, 2008), and cultured at 25° C. under dark for three days. The calluses after cocultivation were placed on the selection medium containing Hm (Hiei and Komari, 2008) for further culture. The proliferated Hm resistant calluses were treated in X-Gluc solution, and their GUS activity was investigated.

Result and Discussion

The result is shown in Table 2.

No Hm resistance or GUS positive callus was obtained from the callus to which the controls, LBA4404 (pLC41GWH-IG), LBA4404 (pIG121Hm), GV2260 (pLC41GWH-IG) and GV3850 (pLC41GWH-IG), were inoculated (Table 2). In comparison, transformed calluses were obtained from all of the super ternary vector strains into which the booster vector pVGW9 has been introduced. In particular, transformed calluses were obtained from 9.6% of the tested callus in LBA4404 (pLC41GWH-IG/pVGW9) (Table 2). It is relatively easy to transform the indica type of rice when an immature embryo is used as the starting material, but it is quite difficult when callus is used as the starting material. It was confirmed that the transformation ability improved just by introducing the booster vector pVGW9 into strains of various binary vector systems that had been conventionally used, and that transformed cells were easily obtained from all strains.

Example 5

Gene Introduction to the Tomato Micro-Tom by Super Ternary Vector System

In the present Example, transgenes were introduced into the tomato Micro-Tom by using the super ternary vector strain of LBA4404 which were constructed in Example 1.

Materials and Method

The seeds of the model variety of tomatoes, Micro-Tom, were sterilized and germinated on agar medium, then the cotyledon from which the true leaf has just begun to sprout was cut off and infected with *Agrobacterium*. The details of the method are as described in Sun et al. (2006). The strains used in the experiment are LBA4404 (pLC41GWH-IG), GV2260 (pLC41GWH-IG) and LBA4404 (pLC41GWH-IG/pVGW7), LBA4404 (pLC41GWH-IG/pVGW9), GV2260 (pLC41GWH-IG/pVGW9), which were prepared in Example 1. Cocultivation was performed at 25° C., under the dark condition for three days. Leaf segments after coculture were treated in X-Gluc solution and the GUS activity was investigated.

Result and Discussion

The result is shown in Table 3.

TABLE 2

Result of Transformation in Callus of Indica Rice IR64 (at the callus level)

| Tested *Agrobacterium* strains (tested vectors) | Inoculated Callus (A) | Callus that produced hygromycin resistance and GUS positive cells (B) | Transformation efficiency at callus level (B/A: %) |
|---|---|---|---|
| GV2260 (pLC41GWH-IG) | 129 | 0 | 0.0 |
| GV2260 (pLC41GWH-IG/pVGW9) | 120 | 1 | 0.8 |
| GV3850 (pLC41GWH-IG) | 125 | 0 | 0.0 |
| GV3850 (pLC41GWH-IG/pVGW9) | 131 | 4 | 3.1 |
| LBA4404 (pLC41GWH-IG) | 138 | 0 | 0.0 |
| LBA4404 (pLC41GWH-IG/pVGW9) | 115 | 11 | 9.6 |
| LBA4404 (pIG121Hm) | 122 | 0 | 0.0 |
| LBA4404 (pIG121Hm/pVGW9) | 131 | 6 | 4.6 |

TABLE 3

Transient GUS activity after cocultivation using cotyledon segments of tomato (Micro-Tom)

| Tested *Agrobacterium* strains (tested vectors) | Addition of acetosyringone (0.1 mM) | Inoculated cotyledon segment (A) | GUS active cotyledon segment (B) | Efficiency (B/A: %) |
|---|---|---|---|---|
| GV2260 (pLC41GWH-IG) | + | 32 | 26 | 81.3 |
| GV2260 (pLC41GWH-IG/pVGW9) | + | 33 | 30 | 90.9 |
| GV2260 (pLC41GWH-IG) | − | 32 | 10 | 31.3 |

TABLE 3-continued

Transient GUS activity after cocultivation using cotyledon segments of tomato (Micro-Tom)

| Tested Agrobacterium strains (tested vectors) | Addition of acetosyring one (0.1 mM) | Inoculated cotyledon segment (A) | GUS active cotyledon segment (B) | Efficiency (B/A: %) |
|---|---|---|---|---|
| GV2260 (pLC41GWH-IG/pVGW9) | − | 32 | 28 | 87.5 |
| LBA4404 (pLC41GWH-IG) | − | 31 | 4 | 12.9 |
| LBA4404 (pLC41GWH-IG/pVGW9) | − | 32 | 32 | 100.0 |
| LBA4404 (pIG121Hm) | − | 48 | 13 | 27.1 |
| LBA4404 (pIG121Hm/pVGW7) | − | 48 | 42 | 87.5 |
| LBA4404 (pIG121Hm/pVGW9) | − | 48 | 48 | 100.0 |

+: addition, −: no addition

By observing the transient expression of GUS gene, it was found that the effect of addition of the booster vector was small when cocultivation was performed under the presence of acetosyringone, but in the experimental plot without acetosyringone, the additional efficacy of the booster vectors pVGW7 and pVGW9 were obvious (Table 3). In particular, GUS activity was observed in all tested cotyledon segments in the super ternary vector system using pVGW9. Micro-Tom has been known as a variety that can be transformed, and it is expected that if the super ternary vector system incorporating the booster vector pVGW9 is used in conventional binary vector strains for Micro-Tom, transformant would be obtained at a high efficiency that is unprecedented.

Example 6

Transformation of Tomato by a Super Ternary Vector System

In this Example, a comparative test was performed concerning efficiency of transgenic callus formation in tomato variety, Micro-Tom, using the super ternary vector strains prepared in Example 1.

Materials and Method

The seeds of the tomato variety, Micro-Tom, was sterilized and placed on a hormone free MS medium containing a highly concentrated (120 g/L) sucrose, and cultured at 25° C. under a lighted condition for five days, to obtain the seeds of germination-ready state. Then, the seeds were transplanted to a hormone free MS medium that does not contain sucrose, and further cultured for further two days to adjust the germinating energy. The middle of a cotyledon that has not completely exited the seed coat was cut out in a rectangle with a scalpel, and used for infection of Agrobacterium. Infection and cocultivation were performed according to the method of Sun et al. (2006). LBA4404 (pLC41GWH-IG), LBA4404 (pLC41GWH-IG/pVGW7), LBA4404 (pLC41GWH-IG/pVGW9) prepared in Example 1 were used as strains. Note that 0.1 mM of acetosyringone was added to the medium for cocultivation. After cocultivation, the leaf segments were transplanted to MS callus induction medium containing 30 g/L sucrose, 3 g/L gellan gum, 1.5 mg zeatin, 50 mg/L hygromycin, 100 mg/L carbenicillin, 250 mg/L cefotaxime. After two weeks of culture at 25° C. under the light condition, the leaf segments were further transplanted to MS callus induction medium of the same composition to be further culture for 2 weeks. After culture, hygromycin resistance calluses formed on cotyledon segment was picked by tweezers and immersed in the X-Gluc solution to investigate the GUS activity. When multiple hygromycin resistance and GUS positive calluses were formed on the same cotyledon segment and apart from each other, they were counted as different transgenic calluses.

Result and Discussion
The result is shown in Table 4.

TABLE 4

Efficiency of Transformed Callus Formation Using Cotyledon Segment of Tomato (Micro-Tom)

| Tested Agrobacterium strains (tested vectors) | Inoculated cotyledon segment (A) | Hygromycin resistant and GUS positive Callus (B) | Efficiency (B/A: %) |
|---|---|---|---|
| LBA4404 (pLC41GWH-IG) | 60 | 15 | 30.0% |
| LBA4404 (pLC41GWH-IG/pVGW7) | 60 | 25 | 41.7% |
| LBA4404 (pLC41GWH-IG/pVGW9) | 60 | 38 | 63.3% |

Of the hygromycin resistant calluses formed on cotyledon segments, 90% or more were transgenic calluses with strong GUS activity. An addition of the booster vector pVGW9 showed an effect of improving the formation efficiency of transformation callus by 2 folds or more. In comparison, the effect of addition of the booster vector pVGW7 was a bit lower at 1.4 folds (Table 4). Accordingly, the higher transformation ability of the strain having the booster vector pVGW9 than the strain having a booster vector pVGW7 was due to the addition of the virD1 gene, the virD2 gene, the virD3 gene, and the virJ gene derived from pTiBo542 to the pVGW9.

SEQUENCE LISTING FREE TEXT

SEQ ID NO: 1 is the DNA sequence of the pVGW9 vector.

SEQ ID NO: 2 is the DNA sequence of the PCR primer pSa5'EcT22I.

SEQ ID NO: 3 is the DNA sequence of the PCR primer M13 (−20) Fw.

SEQ ID NO: 4 is the DNA sequence of the PCR primer pTiBo542:150641Fw.

SEQ ID NO: 5 is the DNA sequence of the PCR primer delD2-3'Rv.

The invention claimed is:

1. An *Agrobacterium* bacterium comprising plasmids (1) to (3) shown below:
   (1) a plasmid comprising the following components:
       (i) the virB gene, the virC gene, the virD1 gene, the virD2 gene, the virD3 gene, the virG gene and the virJ gene of pTiBo542, and
       (ii) an origin of replication;
   (2) a disarmed Ti plasmid or a disarmed Ri plasmid of *Agrobacterium* bacterium; and
   (3) a plasmid having a T-DNA region consisting of a desired DNA;
wherein each of the plasmids (1) to (3) has a replication mechanism that enables a mutual coexistence with each other.

2. The *Agrobacterium* bacterium according to claim 1, wherein the origin of replication (ii) of the plasmid (1) is IncW origin of replication.

3. The *Agrobacterium* bacterium according to either claim 1, wherein the plasmid (1) further comprises the virE gene of pTiBo542.

4. The *Agrobacterium* bacterium according to claim 1, wherein the plasmid (1) further comprises the repA gene.

5. The *Agrobacterium* bacterium according to claim 1, wherein the plasmid (1) further comprises a drug selectable marker gene.

6. The *Agrobacterium* bacterium according to claim 5, wherein the drug selectable marker gene is a gentamicin resistance gene.

7. The *Agrobacterium* bacterium according to claim 1, wherein the plasmid (1) is pVGW9 having a DNA sequence of SEQ ID NO: 1.

8. The *Agrobacterium* bacterium according to claim 1, wherein the disarmed plasmid of the *Agrobacterium* bacterium (2) is a disarmed Ti plasmid.

9. The *Agrobacterium* bacterium according to claim 1 that does not retain a disarmed pTiBo542.

10. The *Agrobacterium* bacterium according to claim 1 that is produced by introducing the plasmid (1) and the plasmid (3) to the *Agrobacterium* bacterium selected from a group consisting of LBA4404, GV3850, GV3TillSE, C58-Z707, GV3101::pMP90, GV3101::pMP90RK, GV2260, and NTI (pKPSF2).

11. A method for plant transformation comprising contacting the *Agrobacterium* bacterium of claim 1 with a plant cell.

12. The method for plant transformation according to claim 11, wherein the plant is an angiosperm.

* * * * *